(12) United States Patent
Shu

(10) Patent No.: US 11,236,090 B2
(45) Date of Patent: Feb. 1, 2022

(54) SUBSTITUTED GLUTARIMIDES AS CDK INHIBITORS

(71) Applicant: SHANGHAI MEIZER PHARMACEUTICALS CO., LTD., Shanghai (CN)

(72) Inventor: Yongzhi Shu, Shanghai (CN)

(73) Assignee: SHANGHAI MEIZER PHARMACEUTICALS CO., LTD., Shanghai (CN)

( * ) Notice: Subject to any disclaimer, the term of this patent is extended or adjusted under 35 U.S.C. 154(b) by 0 days.

(21) Appl. No.: 16/821,845

(22) Filed: Mar. 17, 2020

(65) Prior Publication Data

US 2020/0216450 A1    Jul. 9, 2020

Related U.S. Application Data

(63) Continuation of application No. PCT/CN2018/105713, filed on Sep. 14, 2018.

(30) Foreign Application Priority Data

Sep. 17, 2017 (CN) .......................... 201710837228.X

(51) Int. Cl.
| | |
|---|---|
| A61K 31/4412 | (2006.01) |
| C07D 211/40 | (2006.01) |
| C07D 471/04 | (2006.01) |
| A61P 35/00 | (2006.01) |
| C07D 487/04 | (2006.01) |

(52) U.S. Cl.
CPC ............ C07D 471/04 (2013.01); A61P 35/00 (2018.01); C07D 487/04 (2013.01)

(58) Field of Classification Search
CPC .......................... A61K 31/4412; C07D 211/40
USPC .......................................... 514/348; 546/243
See application file for complete search history.

(56) References Cited

U.S. PATENT DOCUMENTS

2019/0336503 A1* 11/2019 Jin ....................... C12Y 203/02

FOREIGN PATENT DOCUMENTS

| WO | 2014063061 A1 | 4/2014 |
|---|---|---|
| WO | 2016015605 A1 | 2/2016 |
| WO | 2017185031 A1 | 10/2017 |
| WO | 2018106870 A1 | 6/2018 |

OTHER PUBLICATIONS

Jordan, V. C. Nature Reviews: Drug Discovery, 2, 2003, 205.*
Hackam, et al. JAMA, 296(14), 2006, 1731-1732.*
International Search Report and Written Opinion (in English and Chinese) issued in PCT/CN2018/105713, dated Nov. 28, 2018, 21 pages provided.

* cited by examiner

*Primary Examiner* — Douglas M Willis
(74) *Attorney, Agent, or Firm* — Hamre, Schumann, Mueller & Larson, P.C.

(57) ABSTRACT

A compound for inhibiting and degrading cyclin-dependent kinase (CDK) is disclosed. The compound is a substituted glutarimide represented by formula I. The compound can be used in the preparation of drugs for treating diseases related to the activity of the CDK.

Formula I

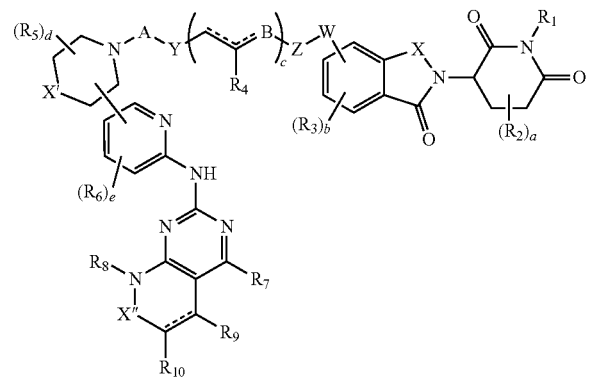

13 Claims, No Drawings

SUBSTITUTED GLUTARIMIDES AS CDK INHIBITORS

TECHNICAL FIELD

The present invention belongs to the field of medicine, and particularly relates to a class of substituted glutarimides inhibiting and degrading cyclin-dependent kinase CDK, a preparation thereof and an application thereof. The compounds of the present invention are useful in the treatment of cell proliferative diseases, such as cancer.

BACKGROUND

Cyclin-dependent kinase (CDK) is a class of serine (Ser)/threonine (T11r) kinase, which is an important signal transduction molecule in cells, and form CDK cyclin complex with cyclin, which is involved in cell growth, proliferation, dormancy, or apoptosis. The CDK family includes CDK 1 to CDK 13, cyclin is divided into cyclin A to cyclin L, and different CDKs are connected to different cyclins respectively.

CDK-specific activation is closely related to the proliferation of some tumors, and abnormal CDK pathway exists in about 80% of human tumors. Multiple reported indications for CDK inhibitors in clinical studies include breast cancer, ovarian epithelial cancer, liposarcoma, non-small cell lung cancer, liver cancer, mantle cell lymphoma, melanoma, multiple myeloma, head neck cancer and other tumors.

CDK inhibitors can also be used to treat various autoimmune system diseases. For example, rheumatoid arthritis is characterized by synovial tissue hyperplasia, and the CDK inhibitor P16 protein can inhibit synovial fibroblasts (Taniguchi k. Et al., Nat Med. 1999, 5: 760-767). CDK inhibitors are effective against other cell proliferation disorders, including psoriasis and lupus, which are characterized by excessive proliferation of keratinocytes.

Therefore, those skilled in the art are dedicated to the development of compounds capable of inhibiting the cyclin-dependent kinase CDK activity.

SUMMARY OF THE INVENTION

The object of the present invention is to provide a compound capable of inhibiting and degrading cyclin-dependent kinase CDK, a preparation thereof and an application thereof.

In the first aspect of the present invention, there is provided a compound represented by the following formula I, or a pharmaceutically acceptable salt thereof:

Formula I

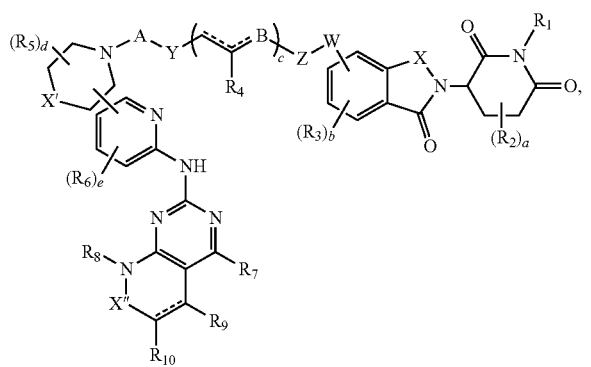

wherein,

——— refers to a single bond;
------- refers to a single or double bond;

A is missing or selected from $C(=O)$, $C(=O)X1$, $SOX1$, $SO_2X1$, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s); wherein X1 is missing or selected from $(CR_{35}R_{36})_kO$, $(CR_{35}R_{36})_kS$ and $NR_{14}$; wherein $R_{35}$, $R_{36}$, $R_{14}$ is each independently selected from H, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s); k is an integer between 0 and 3;

W is missing or selected from O, $NR_{17}$, $—X2C(=O)X3$ and $—X2S(=O)_gX3$; wherein $R_{17}$ is independently H, $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s); wherein X2, X3 is each independently missing or selected from O, S, $NR_{18}$ and $(CH_2)_gO$; wherein g is an integer between 0 and 2; wherein $R_{18}$ is independently H, $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

Y is $(CR_{22}R_{23})_h$, $CHX4(CR_{22}R_{23})_h$, $CX4=CH(CR_{22}R_{23})_h$ or $(CR_{22}R_{23})_h$; wherein h is an integer between 0 and 30; wherein $R_{22}$, $R_{23}$ is each independently selected from H, cyano, hydroxyl, amino, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), and $C_{1-8}$ hydrocarbyloxy group with or without substituent(s); wherein X4 is H, halogen, cyano, nitro, hydroxyl, $C_{1-8}$ hydrocarbyloxy group with or without substituent(s), $C_{1-8}$ hydrocarbyloxycarbonyl group with or without substituent(s), $C_{1-8}$ amino group with or without substituent(s), $C_{1-8}$ ester group with or without substituent(s), $C_{1-8}$ aminocarbonyl group with or without substituent(s), $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

Z is $(CR_{24}R_{25})_i$, $CHX5(CR_{24}R_{25})_i$, $CX5=CH(CR_{24}R_{25})_i$ or $C≡C(CR_{24}R_{25})_i$; wherein i is an integer between 0 and 30; wherein $R_{24}$, $R_{25}$ is each independently selected from H, cyano, hydroxyl, amino, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), and $C_{1-8}$ hydrocarbyloxy group with or without substituent(s); wherein X5 is H, halogen, cyano, nitro, hydroxyl, $C_{1-8}$ hydrocarbyloxy group with or without substituent(s), $C_{1-8}$ hydrocarbyloxycarbonyl group with or without substituent(s), $C_{1-8}$ amino group with or without substituent(s), $C_{1-8}$ ester group with or without substituent(s), $C_{1-8}$ aminocarbonyl group with or without substituent(s), $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

B is missing or selected from O, $C=O$, S, $NR_{15}$, $—NR_{15}C(=O)—$, $—C(=O)NR_{15}—$, $—C(=O)O—$, $OC(=O)O—$, $—NR_{15}C(=O)O—$, $—OC(=O)NR_{15}—$, $—NR_{15}C(=O)NR_{16}—$, $C_{1-12}$ hydrocarbyl group with or without substituent(s), $C_{1-12}$ cyclic hydrocarbyl group with or without substituent(s), and $C_{1-12}$ heterocyclic hydrocarbyl group with or without substituent(s); wherein $R_{15}$, $R_{16}$ is each independently selected from H, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s);

X is selected from $CR_{19}R_{20}$, $C(=O)$, $S(=O)$, $SO_2$, and $NR_{21}$; wherein $R_{19}$, $R_{20}$ is each independently selected from H, cyano, hydroxyl, amino, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), and $C_{1-8}$ hydrocarbyloxy group with or without substituent(s); wherein $R_{21}$ is selected from H, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s);

when X' is missing or when X' is not substituted, X' is selected from NH, $CH_2$, O, S, $C(=O)$, $S(=O)$ and $S(=O)_2$; when X' is substituted, X' is selected from N and CH;

X" is missing or selected from $C(=O)$, $CH_2$, $S(=O)$ and $S(=O)_2$;

$R_1$, $R_8$ is each independently selected from H, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), and $C_{1-6}$ acyl group with or without substituent(s);

$R_2$, $R_5$ is each independently selected from hydrogen, $OR_{26}$, $NR_{27}R_{28}$, cyano, halogen, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), $C_{1-6}$ acyl group with or without substituent(s) and $C_{1-6}$ amido group with or without substituent(s); wherein $R_{26}$, $R_{27}$, $R_{28}$ is each independently selected from H, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s);

$R_3$, $R_6$, $R_7$, $R_9$, $R_{10}$ is each independently selected from H, $OR_{29}$, $NR_{30}R_{31}$, cyano, halogen, nitro, $C_{1-8}$ hydrocarbyl group with or without substituent(s), cyclic hydrocarbyl group with or without substituent(s), heterocyclic hydrocarbyl group with or without substituent(s), $X6S(=O)_jR_{32}$, and $X6C(=O)R_{33}$; wherein j is an integer between 0 to 2; wherein $R_{29}$, $R_{30}$, $R_{31}$, $R_{32}$, $R_{33}$ is each independently selected from H, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s) and amino; wherein X6 is missing or selected from O, S, and $NR_{34}$; wherein $R_{34}$ is H, $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

$R_4$ is selected from H, cyano, carboxyl, $C_{1-8}$ hydrocarbyl group with or without substituent(s), and $C_{1-8}$ hydrocarbyloxy carbonyl group with or without substituent(s);

a is an integer between 0 and 5 (such as 1, 2, 3, 4, 5);

b is an integer between 0 and 3 (such as 1, 2, 3);

c is an integer between 0 and 30 (such as 1, 2, 3, 4, 5, 6, 7, 8, 9);

d is an integer between 0 and 9 (such as 1, 2, 3, 4, 5, 6, 7, 8, 9);

e is an integer between 0 and 3 (such as 1, 2, 3).

In another preferred example, A is missing; W is —X2C(=O)X3, wherein X3 is $NR_{18}$ and X2 is missing, or X2 is $NR_{18}$ and X3 is missing; Y is $(CR_{22}R_{23})_h$, wherein $R_{22}$, $R_{23}$ is each independently selected from H, hydroxyl, and $C_{1-4}$ hydrocarbyl group with or without substituent(s), h is an integer between 1 and 6; Z is $(CR_{24}R_{25})_i$, wherein $R_{24}$, $R_{25}$ is each independently selected from H, hydroxyl, and $C_{1-4}$ hydrocarbyl group with or without substituent(s), i is an integer between 1 and 6; c is 0.

In another preferred example, A is missing; W is missing or O; Y is $(CR_{22}R_{23})_h$, wherein $R_{22}$, $R_{23}$ is each independently selected from H, hydroxyl, and $C_{1-4}$ hydrocarbyl group with or without substituent(s), h is an integer between 0 and 3; B is O; Z is $(CR_{24}R_{25})_i$, wherein $R_{24}$, $R_{25}$ is each independently selected from H, hydroxyl, and $C_{1-4}$ hydrocarbyl group with or without substituent(s), i is an integer between 0 and 3; c is an integer between 1 and 6.

In another preferred example, A is $C(=O)X1$; wherein XI is missing or selected from $(CR_{35}R_{36})_kO$ and $(CR_{35}R_{36})_kS$, wherein k is an integer between 0 and 2; $R_{35}$, $R_{36}$ is each independently H, or $C_{1-4}$ alkyl; W is $NR_{17}$, wherein $R_{17}$ is H, or $C_{1-4}$ hydrocarbyl group with or without substituent(s); Y is $(CR_{22}R_{23})_h$, wherein $R_{22}$, $R_{23}$ is each independently selected from H, hydroxyl, $C_{1-4}$ hydrocarbyl group with or without substituent(s); h is an integer between 0 and 3; Z is $(CR_{24}R_{25})_i$, wherein $R_{24}$, $R_{25}$ is each independently selected from H, hydroxyl, $C_{1-4}$ hydrocarbyl group with or without substituent(s), i is an integer between 0 and 3; B is O; c is an integer between 1 and 4.

In another preferred example, A is $SO_2XI$; wherein XI is missing or selected from O and S; W is O; Y is $(CR_{22}R_{23})_h$, wherein $R_{22}$, $R_{23}$ is each independently selected from H, hydroxyl, and $C_{1-4}$ hydrocarbyl group with or without substituent(s), h is an integer between 1 and 6; Z is $(CR_{24}R_{25})_i$, wherein $R_{24}$, $R_{25}$ is each independently selected from H, hydroxyl, and $C_{1-4}$ hydrocarbyl group with or without substituent(s), i is an integer between 0 and 3; c is 0.

In another preferred example, A is missing; W is $NR_{17}$; wherein $R_{17}$ is H or $C_{1-4}$ hydrocarbyl group with or without substituent(s); Y is $(CR_{22}R_{23})_h$, wherein $R_{22}$, $R_{23}$ is each independently selected from H, hydroxyl, and $C_{1-4}$ hydrocarbyl group with or without substituent(s), h is an integer between 0 and 3; Z is $(CR_{24}R_{25})_i$, wherein $R_{24}$, $R_{25}$ is each independently selected from H, hydroxyl, and $C_{1-4}$ hydrocarbyl group with or without substituent(s), i is an integer between 0 and 4; B is O; c is an integer between 1 and 6.

In another preferred example, A is missing; W is missing or O; Y is $(CR_{22}R_{23})_h$, wherein $R_{22}$, $R_{23}$ is each independently selected from H, hydroxyl, and $C_{1-4}$ hydrocarbyl group with or without substituent(s), h is an integer between 0 and 3; Z is $(CR_{24}R_{25})_i$, wherein $R_{24}$, $R_{25}$ is each independently selected from H, hydroxyl, $C_{1-4}$ hydrocarbyl group with or without substituent(s), i is an integer between 0 and 3; B is O; c is an integer between 1 and 10. In another preferred example, W is —X2C(=O)X3-; wherein X2 is $NR_{18}$; X3 is $(CH_2)_gO$; each of g is an integer between 0 and 2; wherein $R_{18}$ is H, or $C_{1-6}$ hydrocarbyl group with or without substituent(s).

In another preferred example, $R_8$ is selected from $C_{3-8}$ cyclic hydrocarbyl group with or without substituent(s) and $C_{3-8}$ heterocyclic hydrocarbyl group with or without substituent(s).

In another preferred example, $R_{10}$ is $X6C(=O)R_{33}$; wherein X6 is missing or selected from O and $NR_{34}$; wherein $R_{34}$ is H or $C_{1-8}$ hydrocarbyl group with or without substituent(s); $R_{33}$ is selected from H, $C_{1-8}$ hydrocarbyl group with or without substituent(s) and amino (preferably dimethylamino).

In another preferred example, $R_9$ is selected from H, cyano, halogen, nitro, and $C_{1-8}$ hydrocarbyl group with or without substituent(s) (preferably $C_{1-3}$ alkyl). In another preferred example, any of the substituents is selected from the group consisting of halogen, unsubstituted or halogenated $C_1$-$C_6$ alkyl, unsubstituted or halogenated $C_1$-$C_6$ alkoxy, unsubstituted or halogenated $C_2$-$C_6$ alkoxyalkyl, unsubstituted or halogenated $C_3$-$C_8$ cycloalkyl, unsubstituted or halogenated $C_2$-$C_6$ alkylcarbonyl, unsubstituted or halogenated $C_1$-$C_6$ alkylene-hydroxyl, unsubstituted or $C_1$-$C_6$ alkyl substituted amine.

In another preferred example, the structure of the compound is represented by formula I':

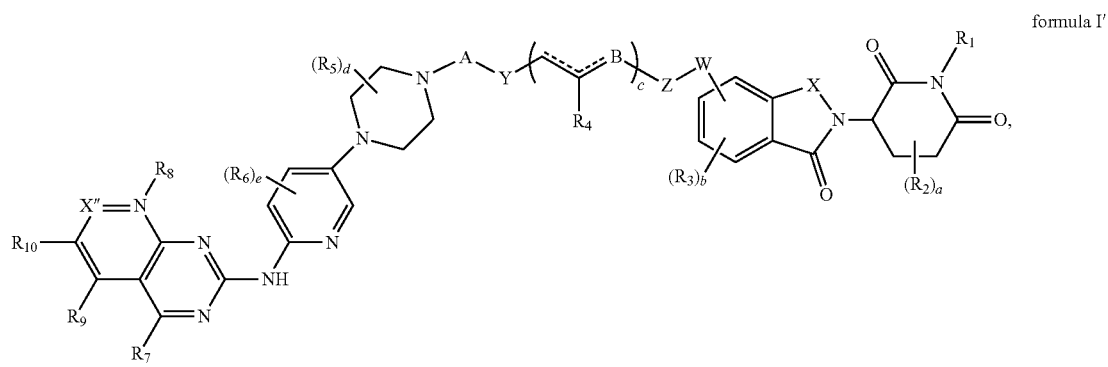

formula I' wherein, each substituent is defined as described above.

In another preferred example, in formula I, or I', ------- refers to a single bond.

In another preferred example, X is C(=O).

In another preferred example, $R_1$, $R_8$ is each independently selected from H, $C_{1-4}$ alkyl with or without substituent(s) and $C_{1-8}$ cycloalkyl with or without substituent(s).

In another preferred example, $R_2$, $R_5$ is each independently selected from hydrogen and $C_{1-4}$ alkyl with or without substituent(s).

In another preferred example, $R_3$ is selected from H and $C_{1-4}$ alkyl with or without substituent(s).

In another preferred example, $R_6$ is selected from hydrogen, $C_{1-4}$ alkyl with or without substituent(s), and $OR_{29}$; wherein $R_{29}$ is selected from H and $C_{1-6}$ alkyl with or without substituent(s).

In another preferred example, $R_7$ is selected from hydrogen and $C_{1-4}$ alkyl with or without substituent(s).

In another preferred example, $R_8$ is selected from H and $C_{3-8}$ cycloalkyl with or without substituent(s).

In another preferred example, $R_9$ is selected from hydrogen and $C_{1-4}$ alkyl with or without substituent(s).

In another preferred example, $R_{10}$ is selected from: halogen, cyano, nitro, $C_{1-4}$ alkyl with or without substituent(s), and C(=O)$NR_{37}R_{38}$, wherein $R_{37}$, $R_{38}$ is each independently selected from H, and $C_{1-4}$ alkyl with or without substituent(s). In another preferred example, $R_4$ is selected from H, cyano and $C_{1-6}$ alkyl with or without substituent(s).

In another preferred example, the structure of the compound is represented by formula I":

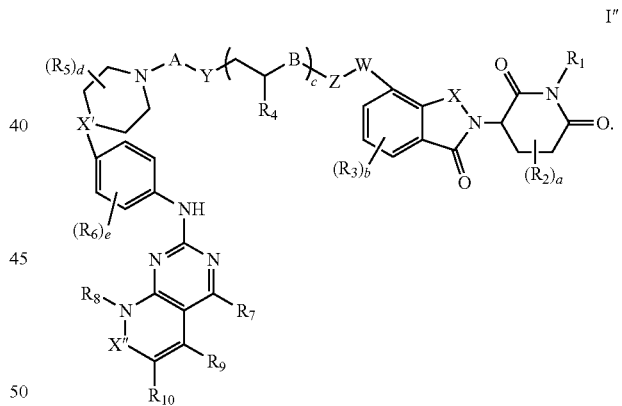

I"

In another preferred example, X' is selected from N and CH in formula I".

In another preferred example, X" is missing or selected from C(=O) and $CH_2$.

In another preferred example, each of the $C_{1-8}$ cyclic hydrocarbyl groups is preferably $C_{3-8}$ cyclic hydrocarbyl group (such as $C_{3-8}$ cycloalkyl). In another preferred example, each of the $C_{1-8}$ heterocyclic hydrocarbyl groups is preferably $C_{3-8}$ heterocyclic hydrocarbyl group (such as $C_{3-8}$ heterocycloalkyl).

In the second aspect of the present invention, there is provided a pharmaceutical composition, which comprises the compound according to the first aspect or a pharmaceutically acceptable salt thereof, or a prodrug thereof, and a pharmaceutically acceptable carrier.

In another preferred example, the effective amount refers to a therapeutically effective amount of an inhibitory effective amount, preferably 0.01 to 99.99%.

In another preferred example, the pharmaceutical composition further comprises one or more other antitumor agents.

In another preferred example, the pharmaceutical composition is used to inhibit the activity of cyclin-dependent kinase CDK.

In another preferred example, the pharmaceutical composition is used for treating diseases related to the activity or expression level of cyclin-dependent kinase CDK.

In the third aspect of the present invention, there is provided a use of the compound according to the first aspect of the present invention for:

(a) preparation of drugs for the treatment of diseases related to the activity or expression level of cyclin-dependent kinase CDK;

(b) preparation of cyclin-dependent kinase CDK targeting inhibitor or degradation agent;

(c) non-therapeutic inhibition or degradation of cyclin-dependent kinase CDK in vitro;

(d) non-therapeutic inhibition of tumor cell proliferation in vitro; and/or (e) treatment of diseases related to the activity or expression level of cyclin-dependent kinase CDK.

In another preferred example, the diseases include tumors, autoimmune diseases, and the like.

In another preferred example, the tumor includes breast cancer, ovarian epithelial cancer, liposarcoma, non-small cell lung cancer, liver cancer, mantle cell lymphoma, melanoma, multiple myeloma, head and neck cancer, and the like.

In another preferred example, the autoimmune disease includes rheumatoid arthritis, psoriasis, systemic lupus erythematosus, multiple sclerosis, organ transplant rejection, and the like.

In the fourth aspect of the present invention, there is provided a method for preparing the compound of formula I according to the first aspect of the present invention, comprising the steps of:

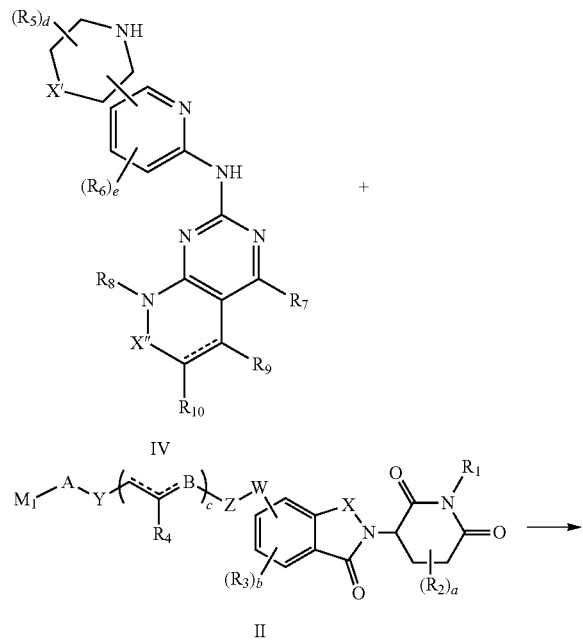

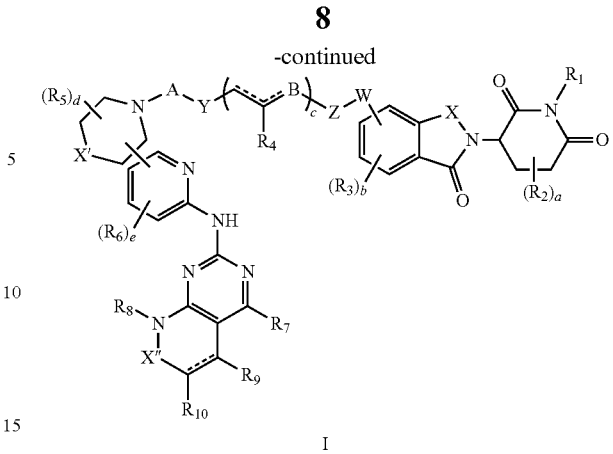

(a) reacting a compound of formula IV and a compound of formula II in an inert solvent to obtain a compound of formula I; in the above formulas, the definition of each group is as described above, and $M_1$ is a leaving group.

In another preferred example, the method further includes the step of:

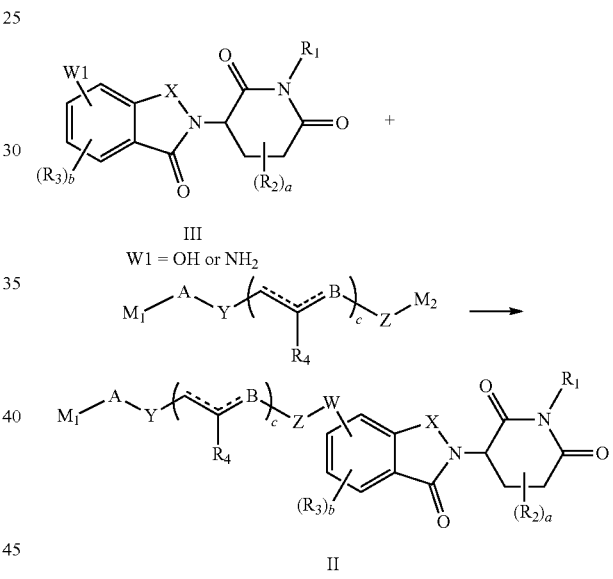

(b) reacting a compound of formula III and a compound of formula V in an inert solvent to obtain a compound of formula II; wherein $M_1$ and $M_2$ are leaving groups.

In the fifth aspect of the present invention, there is provided a method for inhibiting or degrading the activity of cyclin-dependent kinase CDK, comprising the step of administering an inhibitory effective amount of the compound of formula I according to the first aspect of the present invention or a pharmaceutically acceptable salt thereof to an inhibitory subject, or administering an inhibitory effective amount of the pharmaceutical composition according to the fourth aspect of the present invention to an inhibitory subject.

In another preferred example, the inhibition is non-therapeutic inhibition in vitro.

In another preferred example, when an inhibitory effective amount of the compound of formula I according to claim 1 or a pharmaceutically acceptable salt thereof is administered to an inhibitory subject, the inhibitory effective amount is 0.001-500 nmol/L, preferably 0.01-200 nmol/L.

In the sixth aspect of the present invention, there is provided a method for treating a disease related to the activity or expression level of cyclin-dependent kinase CDK, comprising a step of: administering a therapeutically effective amount of the compound of formula I according to the first aspect of the present invention or the pharmaceutical composition according to the fourth aspect of the present invention to a treating subject.

In another preferred example, the subject is a mammal; preferably, the mammal is a human.

In another preferred example, the disease related to the activity or expression level of cyclin-dependent kinase CDK is a tumor or an autoimmune disease.

In the seventh aspect of the present invention, there is provided a method for inhibiting cell proliferation in vitro, comprising: administering an inhibitory effective amount of the compound of formula I according to the first aspect of the present invention or the pharmaceutical composition according to the second aspect of the present invention to an inhibitory subject.

In another preferred example, the cells are tumor cells.

It is to be understood that within the scope of the present invention, the various technical features of the present invention and the various technical features specifically described hereinafter (as in the embodiments) may be combined with each other to form a new or preferred technical solution. Due to space limitations, we will not repeat them here.

DETAILED DESCRIPTION OF THE INVENTION

After extensive and intensive research, the present inventors have prepared a class of compounds having the structure as shown in formula I and found that they have inhibitory and degradation activities to cyclin-dependent kinase CDK. In addition, the compound has an inhibitory effect on cyclin-dependent kinase CDK at a very low concentration, and the inhibitory activity is quite excellent, so it can be used for the treatment of diseases related to the activity or expression level of cyclin-dependent kinase CDK, such as tumors. The present invention has been completed on this basis.

The present invention has disclosed a new class of compounds and their use for inhibiting and degrading cyclin-dependent kinase CDK. These compounds can inhibit and degrade cyclin-dependent kinase CDK and be used to treat non-small cell lung cancer.

Terms

In the present invention, the term "$C_{1-8}$ hydrocarbyl group" refers to a functional group containing only two kinds of atoms of carbon and hydrogen, in which the number of carbon atoms is 1 to 8. A hydrocarbyl group can be regarded as a free radical left after the corresponding hydrocarbon loses one hydrogen atom, which may be an alkyl group, a cycloalkyl group, an alkenyl group, an alkynyl group, etc.; its structure may be linear, branched, or cyclic; and it is aliphatic or aromatic.

The term "$C_{1-6}$ alkyl" refers to a straight or branched alkyl group having 1 to 6 carbon atoms, such as methyl, ethyl, propyl, isopropyl, butyl, isobutyl, sec-butyl, tert-butyl, or similar groups.

The term "alkoxy" as used herein includes O-alkyl, in which "alkyl" is as defined above.

The term "halo" as used herein, unless otherwise indicated, includes fluoro, chloro, bromo or iodo.

The compound of the present invention may contain a double bond. When such double bonds are contained, the compounds of the present invention exist in cis form, trans form or mixtures thereof.

The halogens described herein include fluorine, chlorine, bromine and iodine.

Unless otherwise indicated, the alkyl and alkyl moieties of the alkoxy group herein may be linear, branched, or cyclic.

In the present invention, the term "cyclic hydrocarbyl group" refers to a functional group containing two kinds of atoms of carbon and hydrogen, and includes cycloalkyl, cycloalkenyl (containing at least one carbon-carbon double bond), and aryl. They may be monocyclic, bicyclic or polycyclic. They may be spiro rings or fused rings.

In the present invention, the term "heterocyclic hydrocarbyl group" refers to a functional group containing carbon, hydrogen, and at least one heteroatom other than carbon and hydrogen. It includes heterocycloalkyl, heterocycloalkenyl (containing at least one carbon-carbon double bond), and heteroaryl. One or more ring-forming atoms in the ring are heteroatoms. The heteroatoms can be O, N, S, or any combination thereof. They may be monocyclic, bicyclic or polycyclic. They may be spiro rings or fused rings.

In the present invention, the term "substituent" includes, but is not limited to, fluorine, chlorine, bromine, cyano, hydroxyl, amino, $C_{1-6}$ hydrocarbyloxy group, $C_{1-6}$ halohydrocarbyl group, $C_{1-6}$ acyl group, and $C_{1-6}$ sulfonyl group.

The term "hydrocarbyloxy group" as used herein refers to an O-hydrocarbyl group, where the "hydrocarbyl group" is as defined above.

The term "hydrocarbyloxycarbonyl group" as used herein refers to a C(=O)O-hydrocarbyl group, in which the "hydrocarbyl group" is as defined above.

The term "amino group" as used herein refers to N(H or hydrocarbyl group 1) (H or hydrocarbyl group 2), in which the "hydrocarbyl group" is as defined above, such as —N($C_{1-6}$ alkyl) ($C_{1-6}$ alkyl).

The term "aminocarbonyl group" as used herein refers to a C(=O)-amino group, in which the "amino group" is as defined above.

The term "amido group" as used herein refers to N(H or hydrocarbyl group)-C(=O)-hydrocarbyl group, in which the "hydrocarbyl group" is as defined above.

In the present invention, the term "containing", "comprising" or "including" means that various ingredients can be used together in the mixture or composition of the present invention. Thus, the terms "consisting essentially of" and "consisting of" are included in the term "containing".

In the present invention, the term "pharmaceutically acceptable" ingredient refers to a substance suitable for human and/or animals without excessive adverse side effects (such as toxicity, irritation and allergy), which means it has a reasonable benefit/risk ratio.

In the present invention, the term "effective amount" refers to an amount of a therapeutic agent to treat, alleviate or prevent a target disease or condition, or an amount that exhibits a detectable therapeutic or preventive effect. The exact effective amount for a subject will depend on the subject's size and health, the nature and extent of the condition, and the therapeutic agent and/or combination of therapeutic agents chosen for administration. Therefore, it is not useful to specify an accurate effective amount in advance. However, for a given condition, routine experimentation can be used to determine the effective amount, which can be determined by the clinician. As used herein, unless specifically stated, the term "substituted" refers to the replacement of one or more hydrogen atoms on a group with a substituent selected from the group consisting of: halogen, unsubstituted or halogenated $C_{1-6}$ alkyl, unsubstituted or halogenated $C_{2-6}$ acyl, unsubstituted or halogenated $C_{1-6}$ alkyl-hydroxy. Unless otherwise specified, all compounds present in the present invention are intended to include all possible optical isomers, such as a single chiral compound, or a mixture of various chiral compounds (i.e., a racemate). Among all the compounds of the present invention, each chiral carbon atom may optionally be in the R configuration or the S configuration, or a mixture of the R configuration and the S configuration. As used herein, the term "compound of the present invention" refers to a compound of formula I. The term also includes various crystalline forms, pharmaceutically acceptable salts, hydrates or solvates of the compounds of formula I. As used herein, the term "pharmaceutically acceptable salt" refers to a salt of a compound of the present invention with an acid or a base suitable for use as a drug. The pharmaceutically acceptable salts include inorganic and organic salts. One preferred kind of salts is salts of a compound of the present invention with an acid. Suitable acids for forming salts include, but are not limited to, inorganic acids such as hydrochloric acid, hydrobromic acid, hydrofluoric acid, sulfuric acid, nitric acid, phosphoric acid, etc., organic acids such as formic acid, acetic acid, propionic acid, oxalic acid, malonic acid, succinic acid, fumaric acid, maleic acid, lactic acid, malic acid, tartaric acid, citric acid, picric acid, methanesulfonic acid, benzylsulfonic acid, benzenesulfonic acid, etc.; and acidic amino acids such as aspartic acid, glutamic acid, etc.

Compounds and Pharmaceutically Acceptable Salts Thereof

The present invention relates to a compound of formula I shown as below or a pharmaceutically acceptable salt thereof;

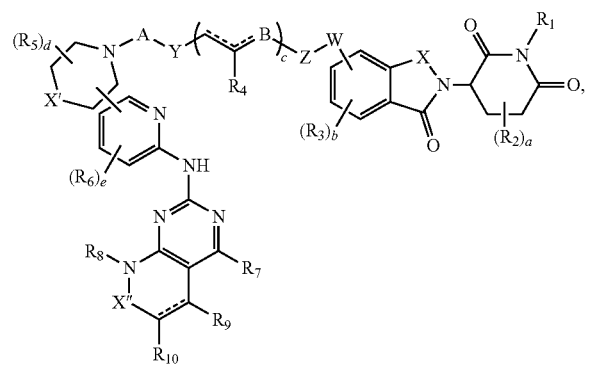

wherein,
——— refers to a single bond;
------- refers to a single or double bond;

A is missing or selected from C(=O), C(=O)X1, SOX1, SO$_2$X1, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s); wherein X1 is missing or selected from $(CR_{35}R_{36})_kO$, $(CR_{35}R_{36})_kS$ and $NR_{14}$; wherein $R_{35}$, $R_{36}$, $R_{14}$ is each independently selected from H, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s); k is an integer between 0 and 3;

W is missing or selected from O, $NR_{17}$, —X2C(=O)X3, and —X2S(=O)$_g$X3; wherein $R_{17}$ is H, $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s); wherein X2, X3 is each independently missing or selected from O, S, and $NR_{18}$; wherein g is an integer between 0 and 2; wherein $R_{18}$ is H, $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

Y is $(CR_{22}R_{23})_h$, $CHX4(CR_{22}R_{23})_h$, $CX4=CH(CR_{22}R_{23})_h$ or $(CR_{22}R_{23})_h$; wherein h is an integer between 0 and 30; wherein $R_{22}$, $R_{23}$ is each independently selected from H, cyano, hydroxyl, amino, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), and $C_{1-8}$ hydrocarbyloxy group with or without substituent(s); wherein X4 is H, halogen, cyano, nitro, hydroxyl, $C_{1-8}$ hydrocarbyloxy group with or without substituent(s), $C_{1-8}$ hydrocarbyloxycarbonyl group with or without substituent(s), $C_{1-8}$ amino group with or without substituent(s), $C_{1-8}$ ester group with or without substituent(s), $C_{1-8}$ aminocarbonyl group with or without substituent(s), $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

Z is $(CR_{24}R_{25})_i$, $CHX5(CR_{24}R_{25})_i$, $CX5=CH(CR_{24}R_{25})_i$ or $C≡C(CR_{24}R_{25})_i$; wherein i is an integer between 0 and 30; wherein $R_{24}$, $R_{25}$ is each independently selected from H, cyano, hydroxyl, amino, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), and $C_{1-8}$ hydrocarbyloxy group with or without substituent(s); wherein X5 is H, halogen, cyano, nitro, hydroxyl, $C_{1-8}$ hydrocarbyloxy group with or without substituent(s), $C_{1-8}$ hydrocarbyloxycarbonyl group with or without substituent(s), $C_{1-8}$ amino group with or without substituent(s), $C_{1-8}$ ester group with or without substituent(s), $C_{1-8}$ aminocarbonyl group with or without substituent(s), $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

B is missing or selected from O, C=O, S, $NR_{15}$, —$NR_{15}$C(=O)—, —C(=O)$NR_{15}$—, —C(=O)O—, OC(=O)O—, —$NR_{15}$C(=O)O—, —OC(=O)$NR_{15}$—, —$NR_{15}$C(=O)$NR_{16}$—, $C_{1-12}$ hydrocarbyl group with or without substituent(s), $C_{1-12}$ cyclic hydrocarbyl group with or without substituent(s), and $C_{1-12}$ heterocyclic hydrocarbyl group with or without substituent(s); wherein $R_{15}$, $R_{16}$ is each independently selected from H, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s);

X is selected from $CR_{19}R_{20}$, C(=O), S(=O), SO$_2$, and $NR_{21}$; wherein $R_{19}$, $R_{20}$ is each independently selected from H, cyano, hydroxyl, amino, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), and $C_{1-8}$ hydrocarbyloxy group with or without substituent(s); wherein $R_{21}$ is selected from H, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s);

when X' is missing or when X' is not substituted, X' is selected from NH, $CH_2$, O, S, C(=O), S(=O) and S(=O)$_2$; when X' is substituted, X' is selected from N and CH;

X" is missing or selected from C(=O), $CH_2$, S(=O) and S(=O)$_2$;

$R_1$, $R_8$ is each independently selected from H, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s) and $C_{1-6}$ acyl group with or without substituent(s);

$R_2$, $R_5$ is each independently selected from hydrogen, $OR_{26}$, $NR_{27}R_{28}$, cyano, halogen, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s), $C_{1-6}$ acyl group with or without substituent(s) and $C_{1-6}$ amido group with or without substituent(s); wherein $R_{26}$, $R_{27}$, $R_{28}$ is each independently selected from H, $C_{1-8}$ hydrocarbyl group with or without substituent(s), $C_{1-8}$ cyclic hydrocarbyl group with or without substituent(s), and $C_{1-8}$ heterocyclic hydrocarbyl group with or without substituent(s);

$R_3$, $R_6$, $R_7$, $R_9$, $R_{10}$ is each independently selected from H, $OR_{29}$, $NR_{30}R_{31}$, cyano, halogen, nitro, $C_{1-8}$ hydrocarbyl group with or without substituent(s), cyclic hydrocarbyl group with or without substituent(s), heterocyclic hydrocarbyl group with or without substituent(s), X6S(=O)$_j R_{32}$, X6C(=O)$R_{33}$; wherein j is an integer between 0 to 2; wherein $R_{29}$, $R_{30}$, $R_{31}$, $R_{32}$, $R_{33}$ is each independently selected from H, $C_{1-8}$ hydrocarbyl group with or without substituent(s), $C_{1-8}$ cyclic hydrocarbyl group with or without substituent(s), $C_{1-8}$ heterocyclic hydrocarbyl group with or without substituent(s) and amino; wherein X6 is missing or selected from O, S, and $NR_{34}$; wherein $R_{34}$ is H, $C_{1-8}$ hydrocarbyl group with or without substituent(s), $C_{1-8}$ cyclic hydrocarbyl group with or without substituent(s), or $C_{1-8}$ heterocyclic hydrocarbyl group with or without substituent(s);

$R_4$ is selected from H, cyano, carboxyl, $C_{1-8}$ hydrocarbyl group with or without substituent(s), and $C_{1-8}$ hydrocarbyloxy carbonyl group with or without substituent(s);

a is an integer between 0 and 5 (such as 1, 2, 3, 4, 5);

b is an integer between 0 and 3 (such as 1, 2, 3);

c is an integer between 0 and 30 (such as 1, 2, 3, 4, 5, 6, 7, 8, 9);

d is an integer between 0 and 9 (such as 1, 2, 3, 4, 5, 6, 7, 8, 9);

e is an integer between 0 and 3 (such as 1, 2, 3).

In another preferred example, each of the $C_{1-8}$ cyclic hydrocarbyl groups is preferably a $C_{3-8}$ cyclic hydrocarbyl group (such as a $C_{3-8}$ cycloalkyl).

In another preferred example, each of the $C_{1-8}$ heterocyclic hydrocarbyl group is preferably $C_{3-8}$ heterocyclic hydrocarbyl group (such as a 4 to 10-membered heterocycloalkyl having 3-8 carbon atoms).

In a preferred embodiment of the invention, the compound is selected from the group consisting of:

| No. | Structure |
|---|---|
| 3 | 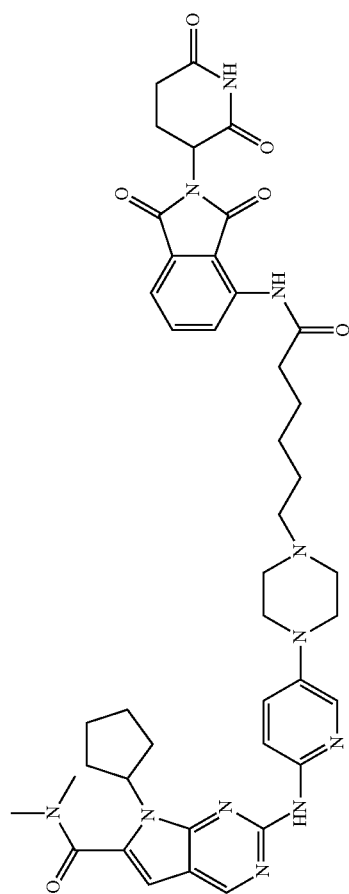 |
| 8 | 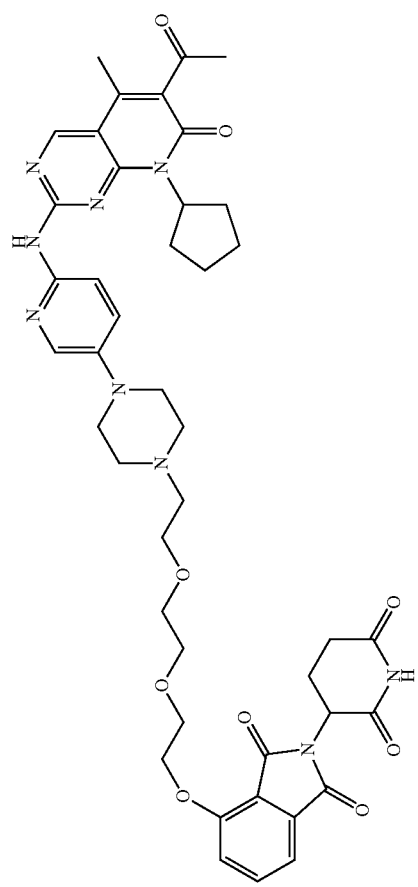 |

-continued
| No. | Structure |
|---|---|
| 11 | 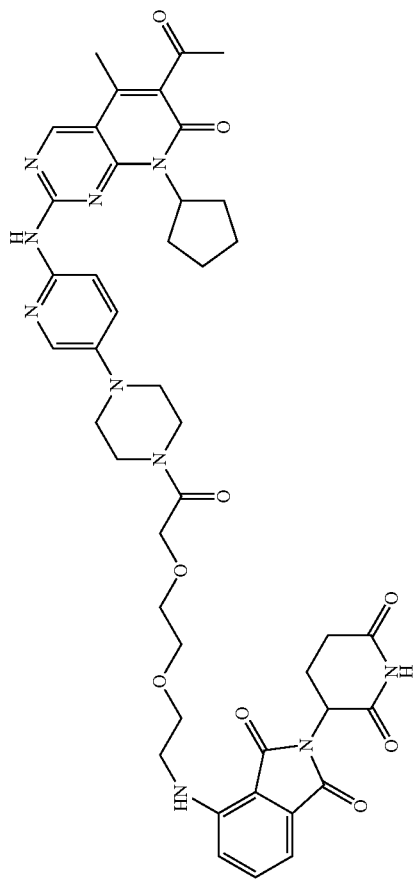 |
| 14 | 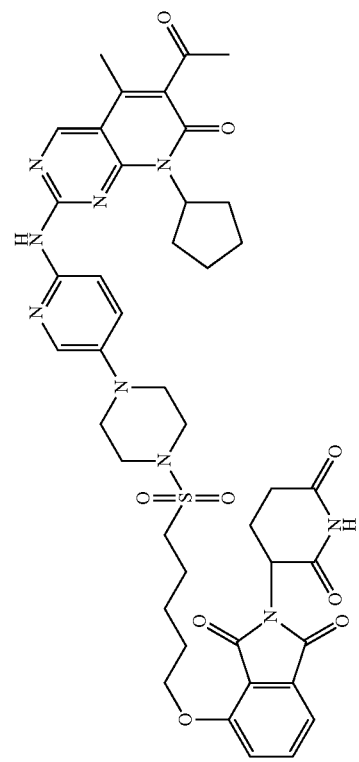 |

-continued
| No. | Structure |
|---|---|
| 15 | 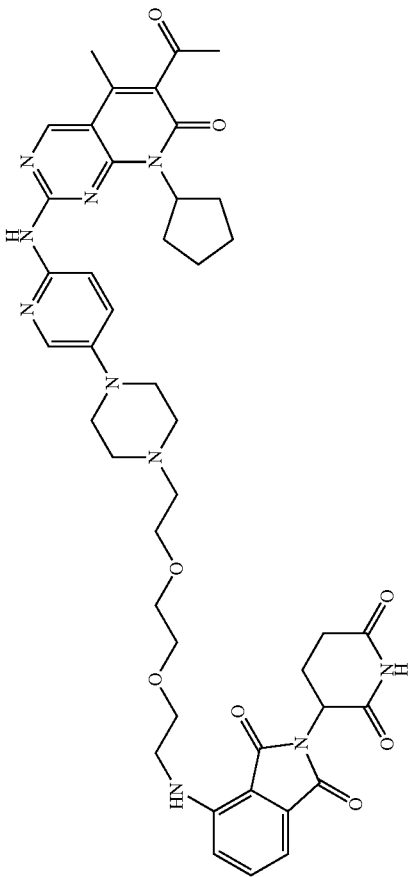 |
| 16 | 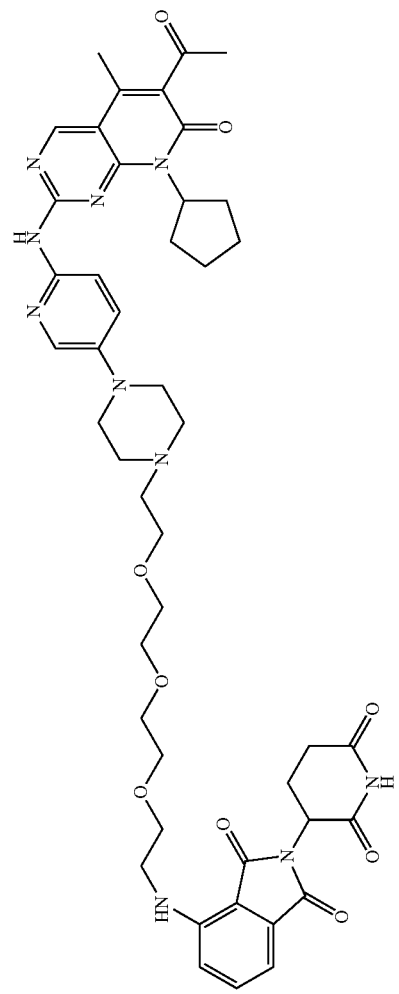 |

-continued
| No. | Structure |
|---|---|
| 17 | 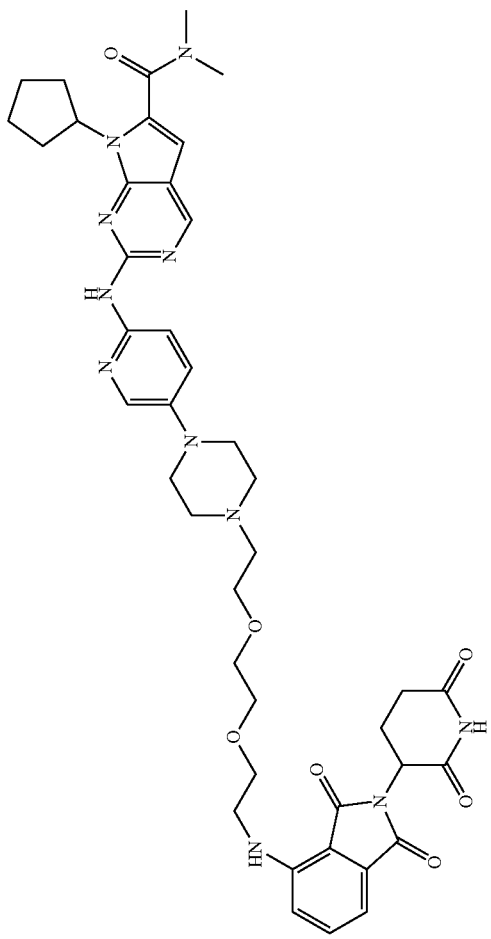 |
| 18 | 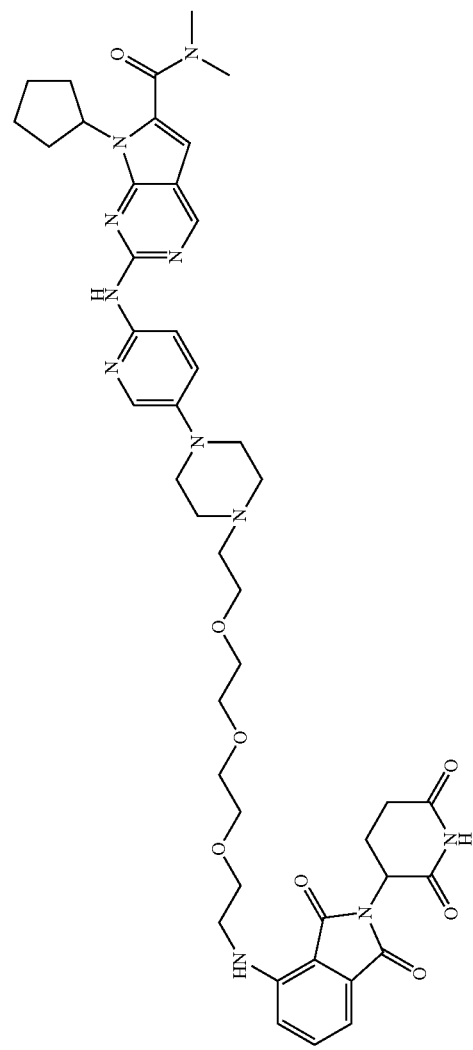 |

-continued
| No. | Structure |
|---|---|
| 19 | 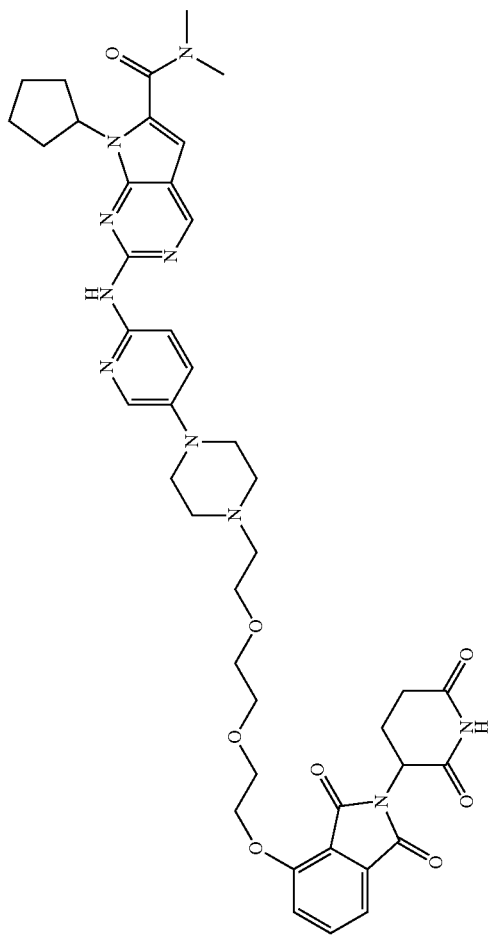 |
| 20 | 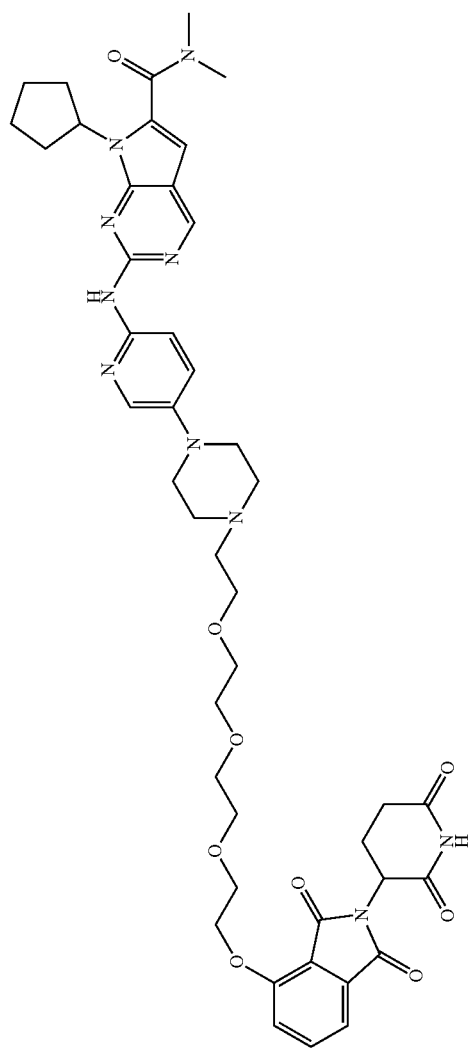 |

-continued
| No. | Structure |
|-----|-----------|
| 21 | 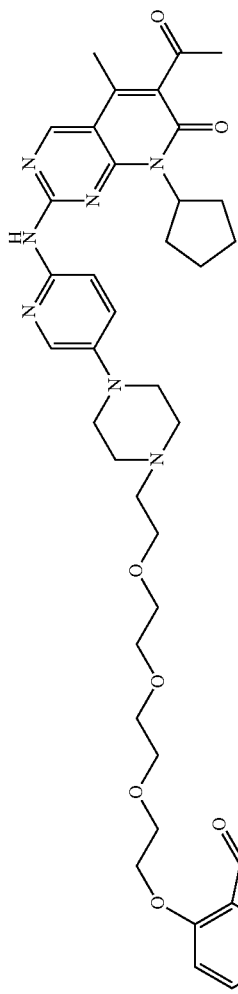 |
| 23 | 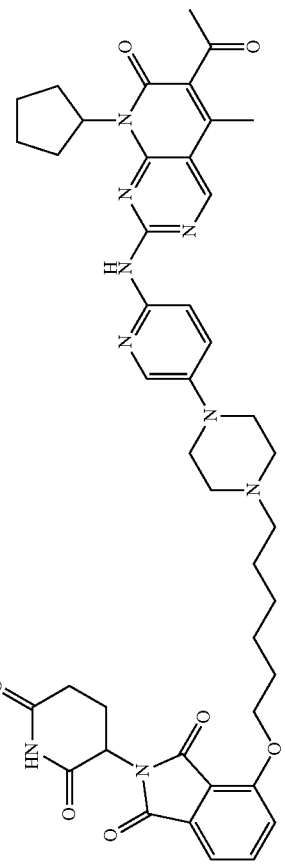 |
| 24 | 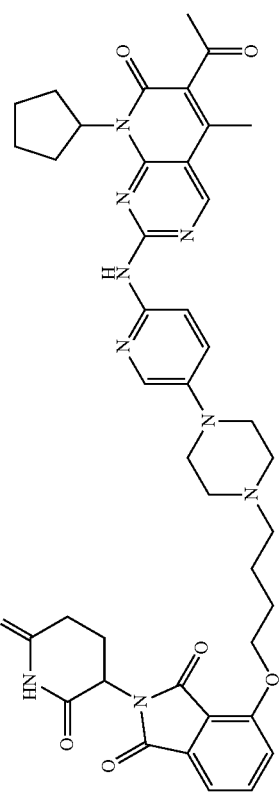 |

-continued
| No. | Structure |
|---|---|
| 25 | 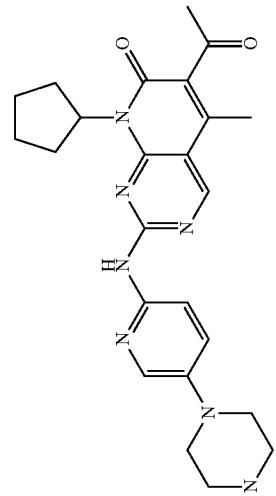 |
| 26 | 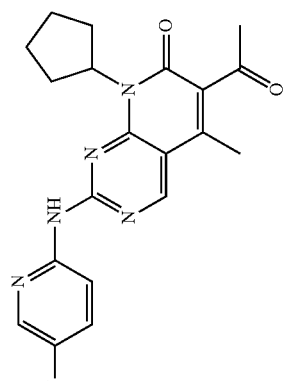 |
| 27 | 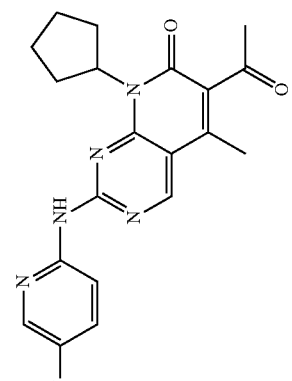 |

-continued
| No. | Structure |
|---|---|
| 28 | 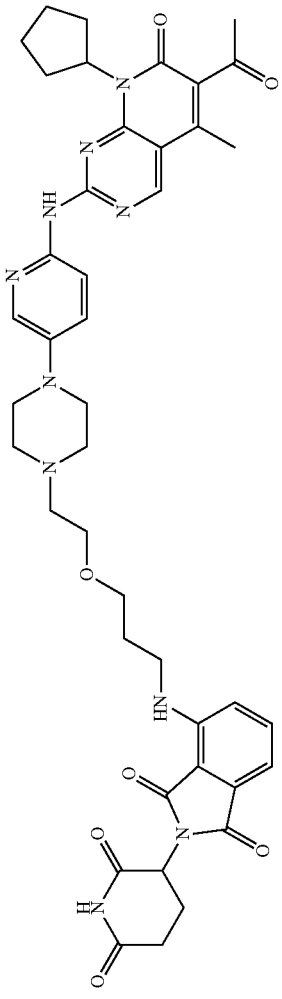 |
| 29 | 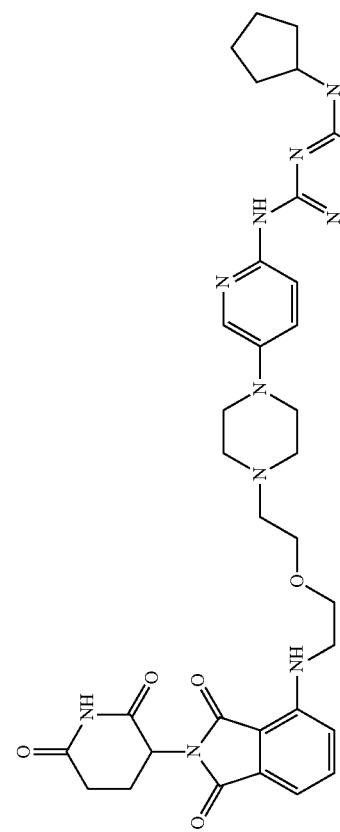 |
| 30 | 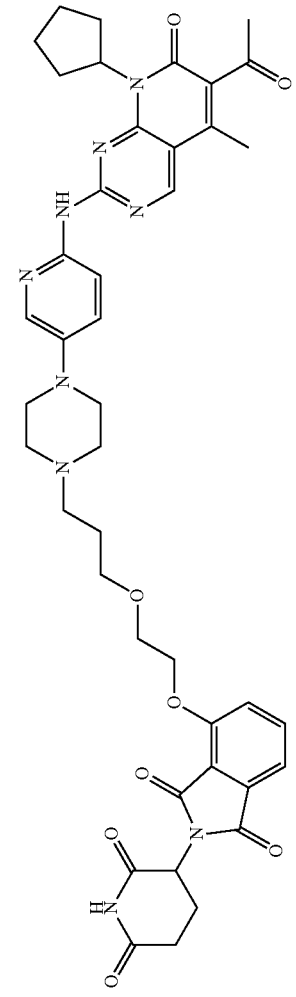 |

| No. | Structure |
|---|---|
| 31 | 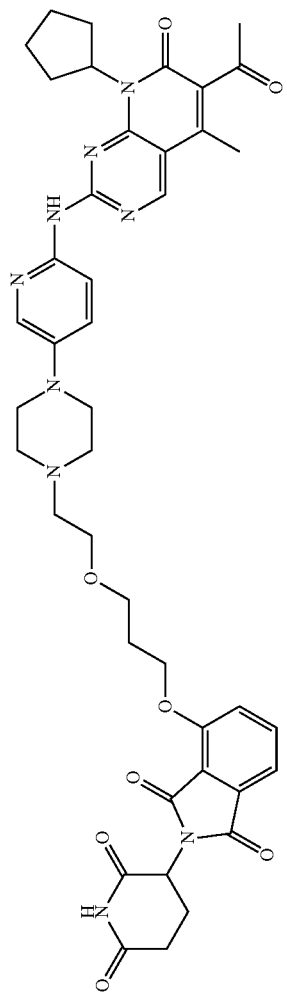 |
| 32 | 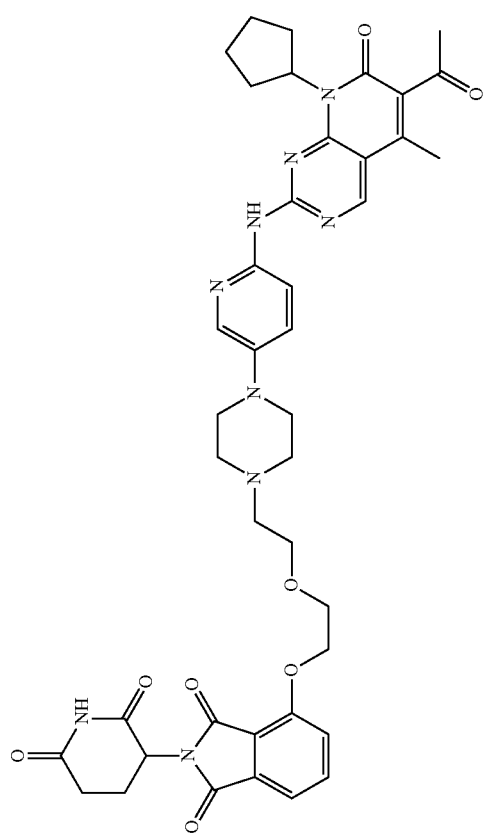 |

| No. | Structure |
|---|---|
| 33 | 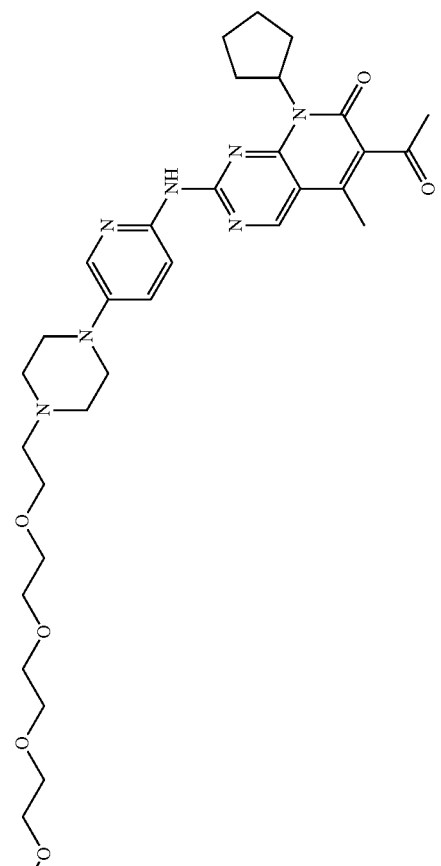 |

-continued
| No. | Structure |
|---|---|
| 34 | 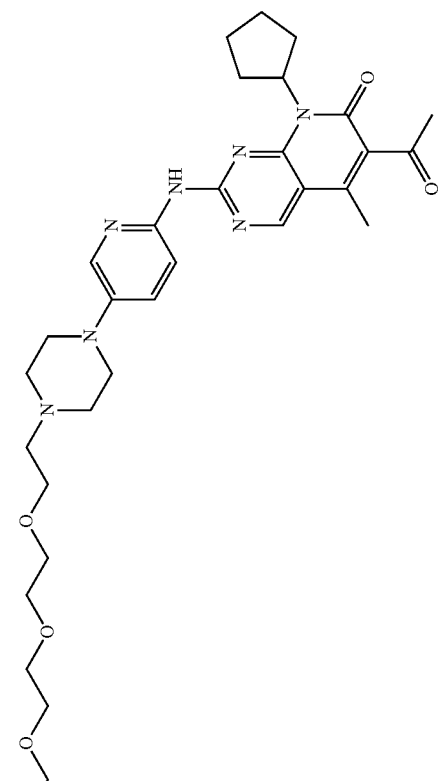 |
| 35 | 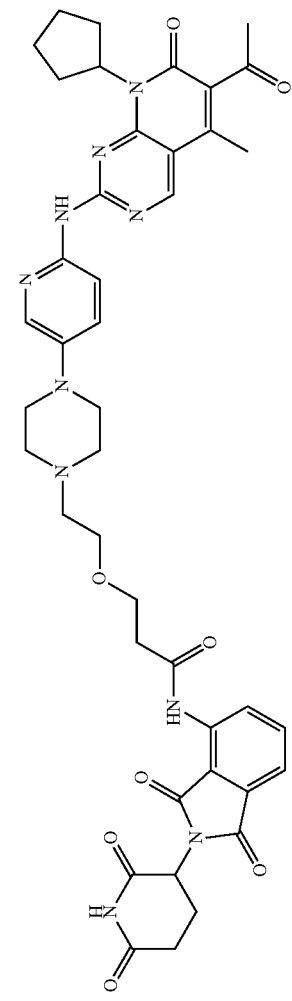 |

-continued
| No. | Structure |
|---|---|
| 36 | 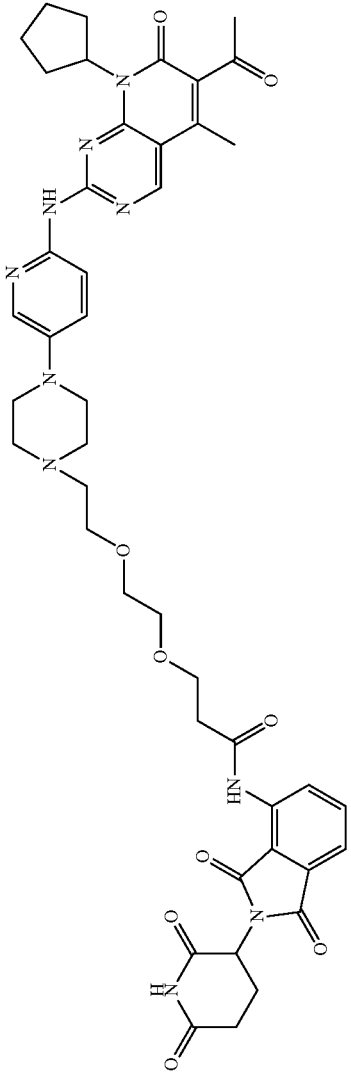 |
| 37 | 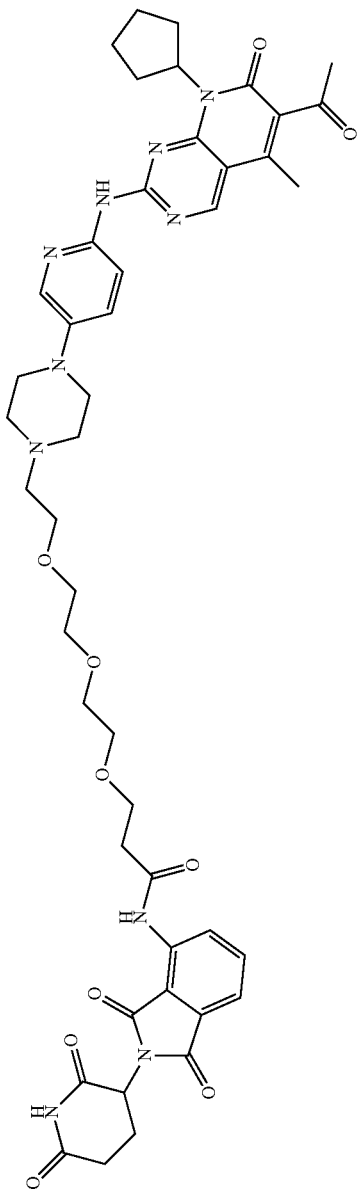 |
| 38 | 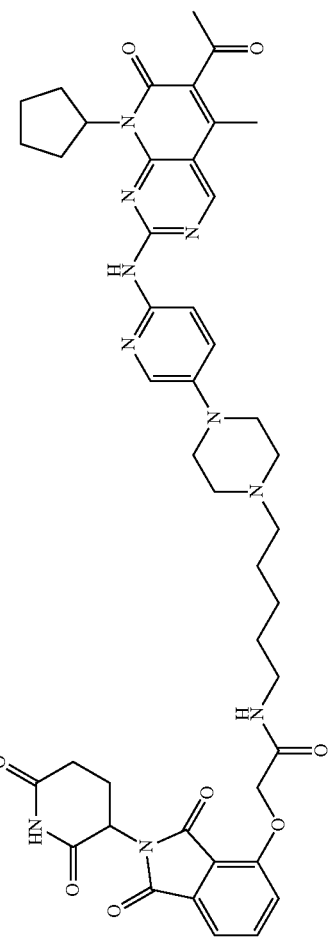 |

-continued
| No. | Structure |
|---|---|
| 39 | 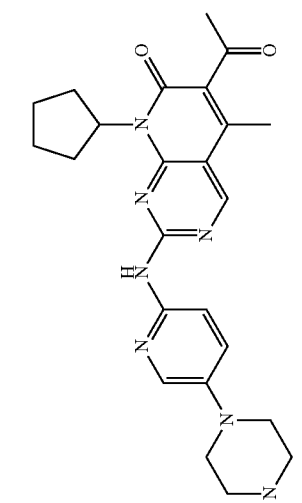 |
| 40 | 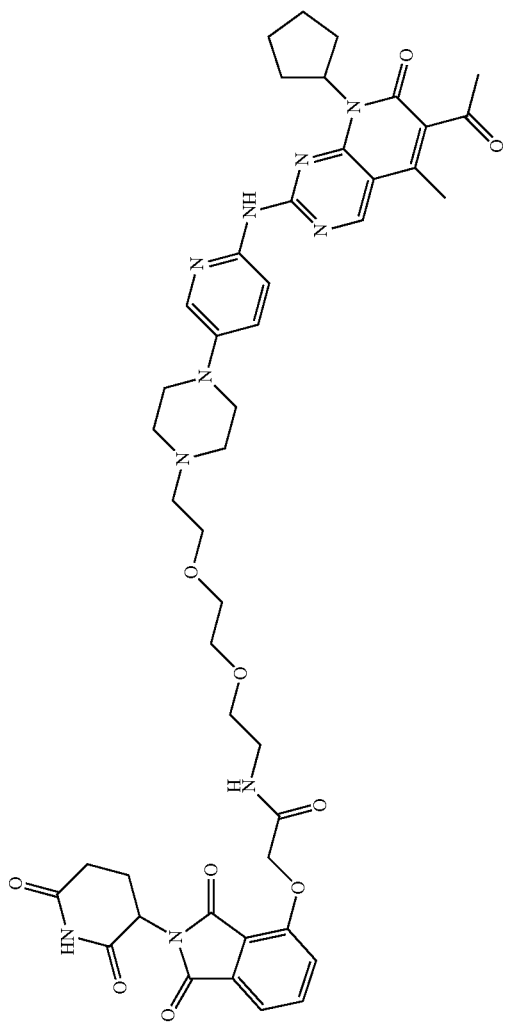 |

-continued
| No. | Structure |
|---|---|
| 41 | 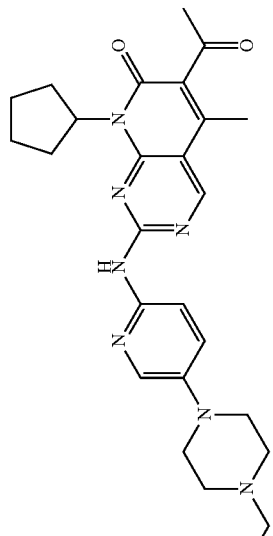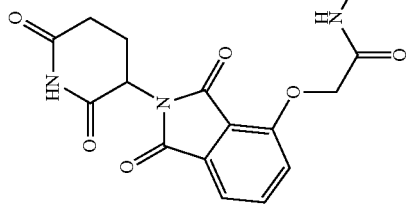 |
| 42 | 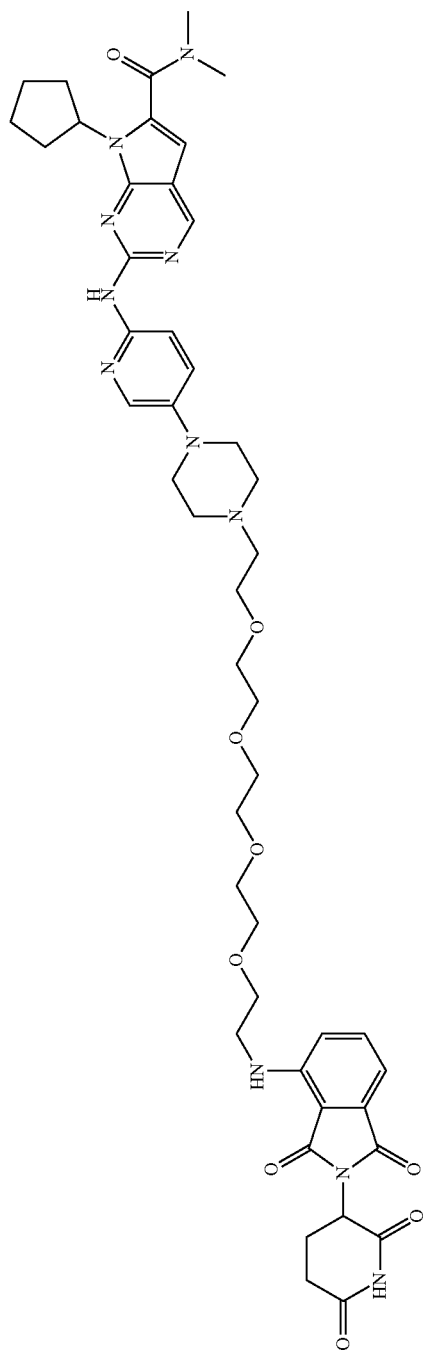 |

-continued
| No. | Structure |
|---|---|
| 43 | 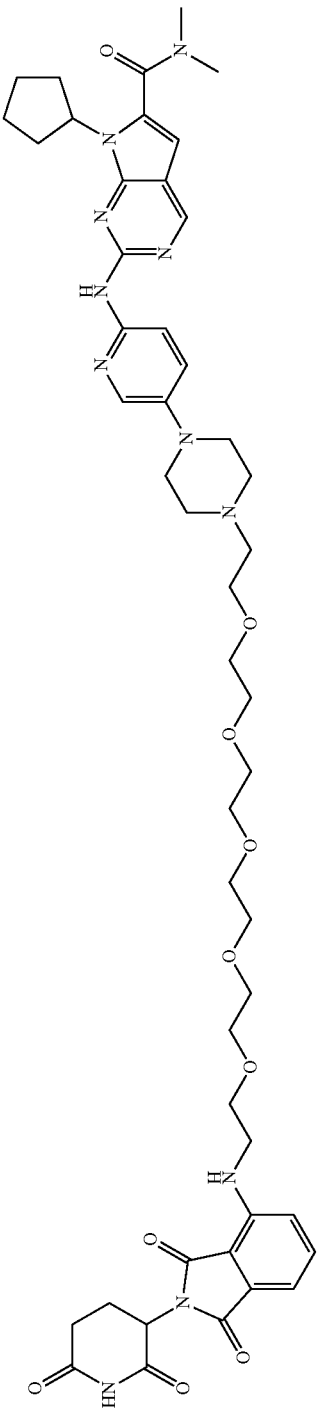 |
| 44 | 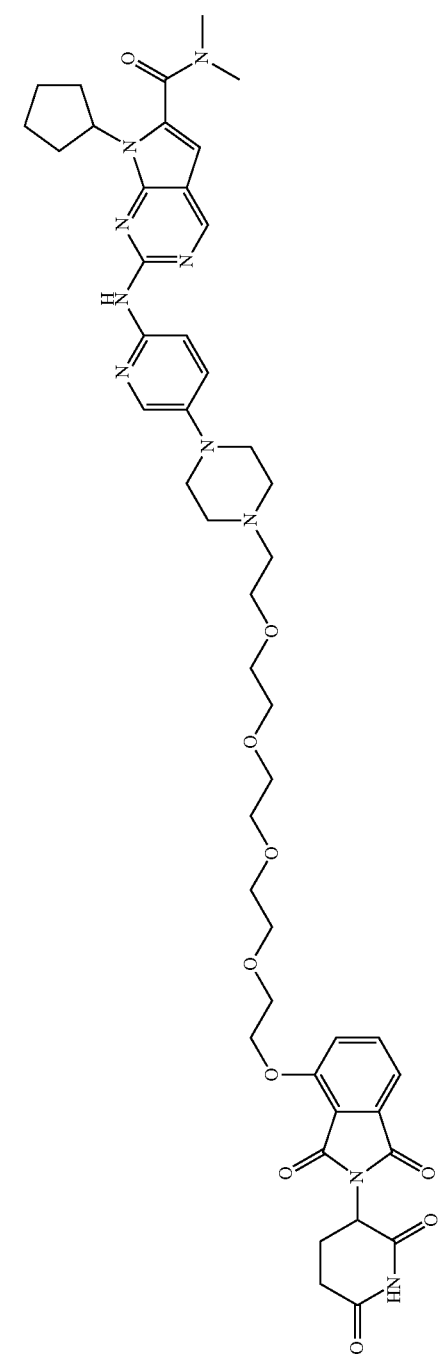 |

-continued
| No. | Structure |
|---|---|
| 45 | 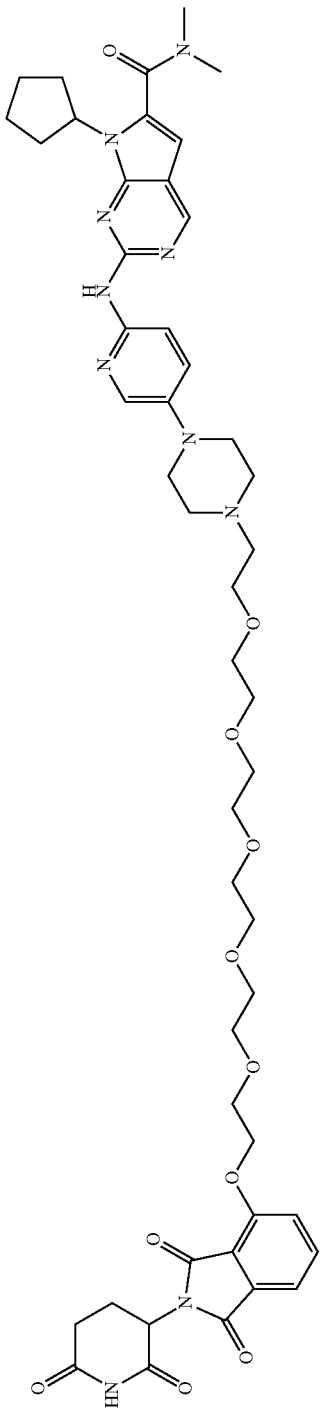 |
| 46 | 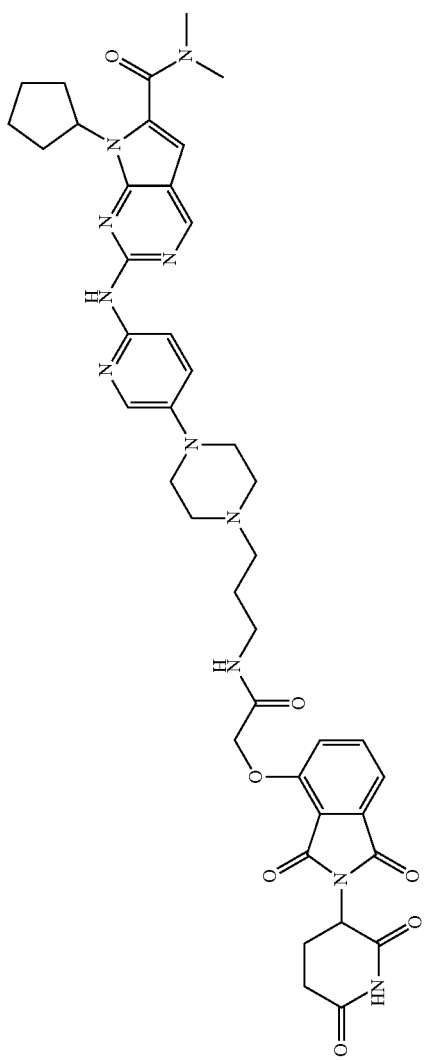 |

| No. | Structure |
|---|---|
| 47 | 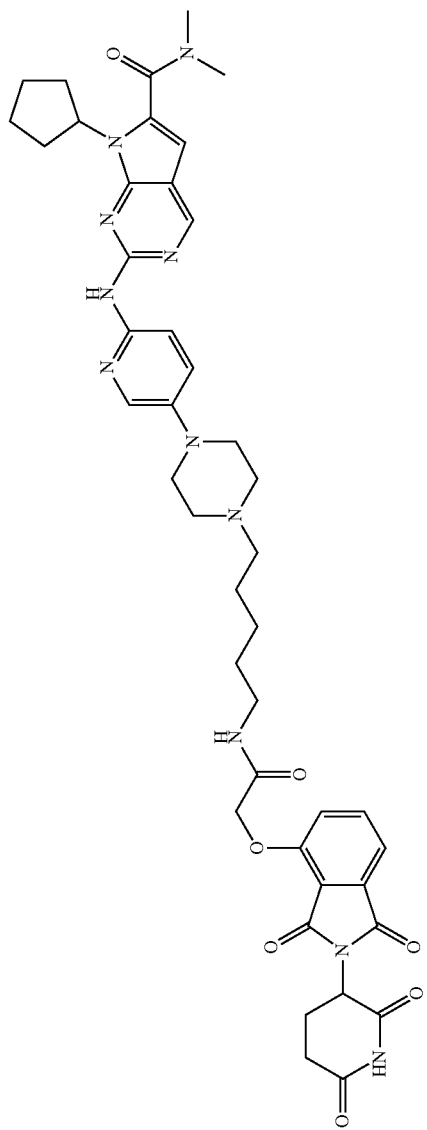 |
| 48 | 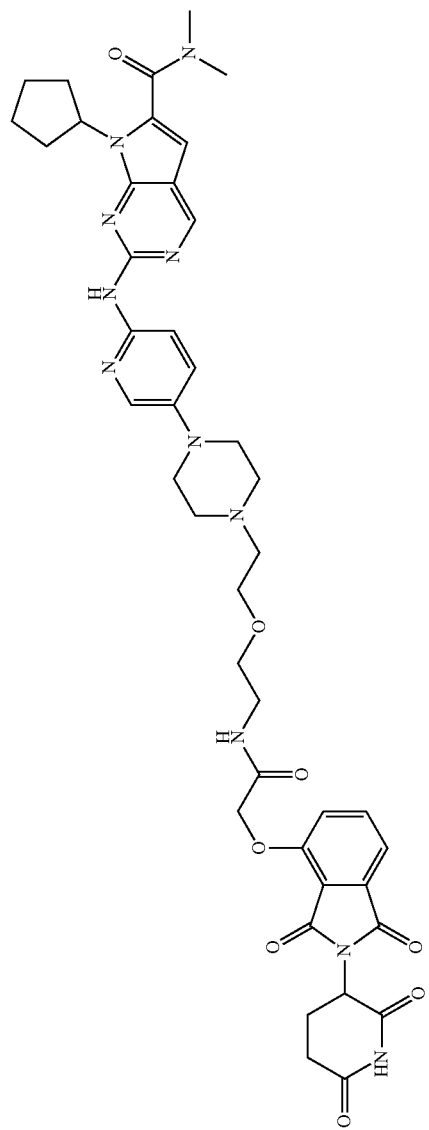 |

-continued
| No. | Structure |
|---|---|
| 49 | 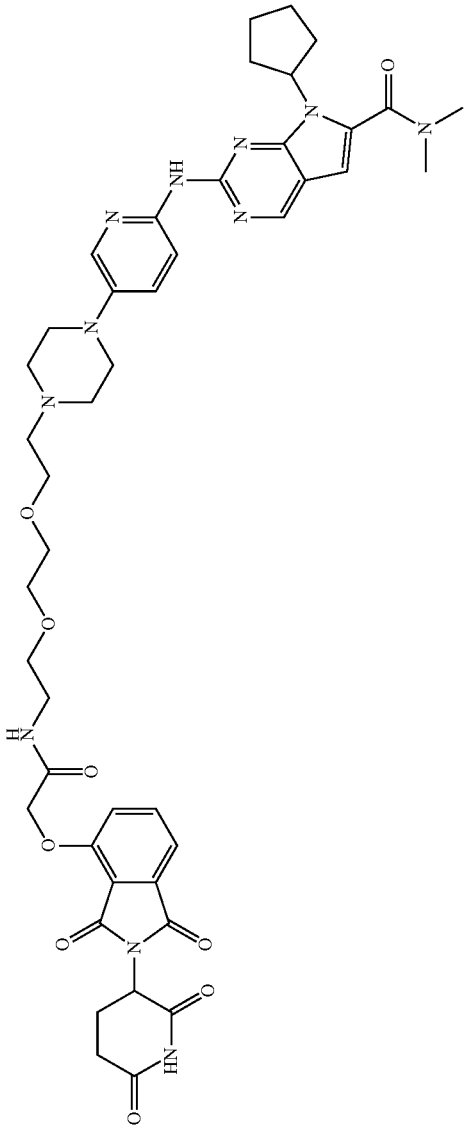 |
| 50 | 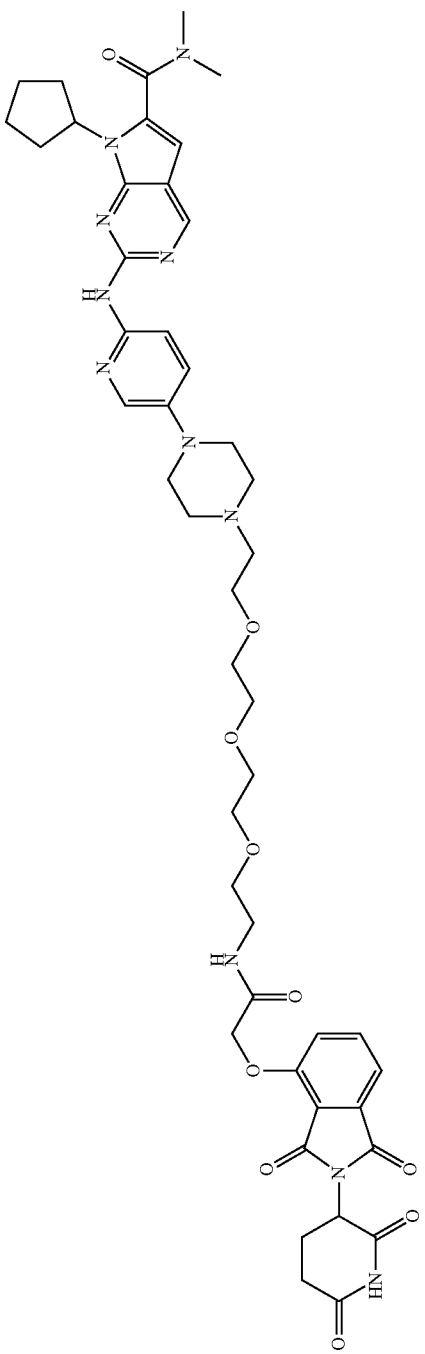 |

-continued
| No. | Structure |
|---|---|
| 51 | 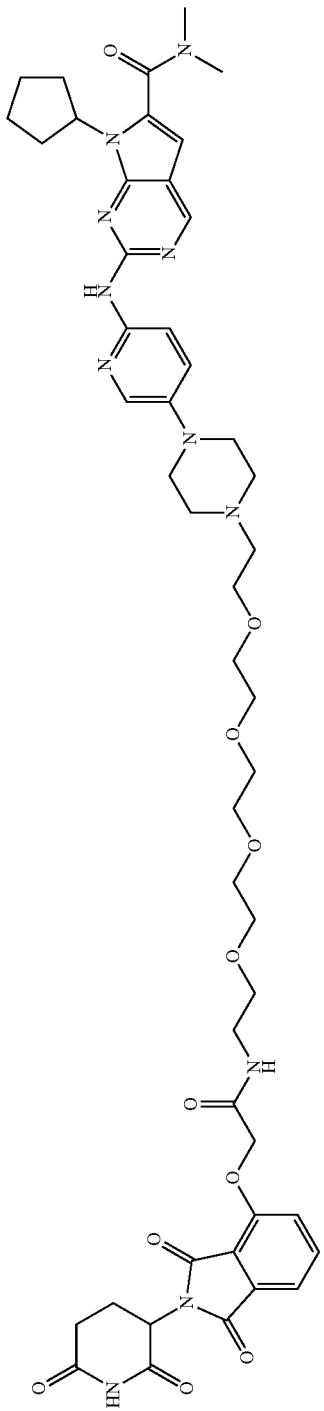 |
| 52 | 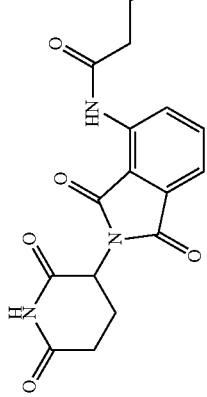 |
| 53 | 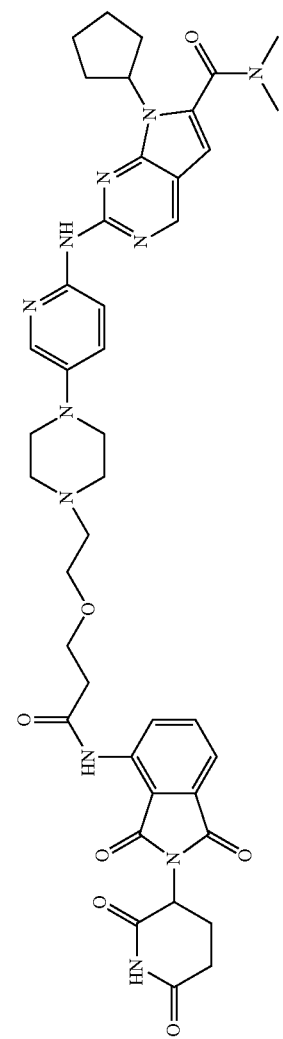 |

| No. | Structure |
|---|---|
| 54 | 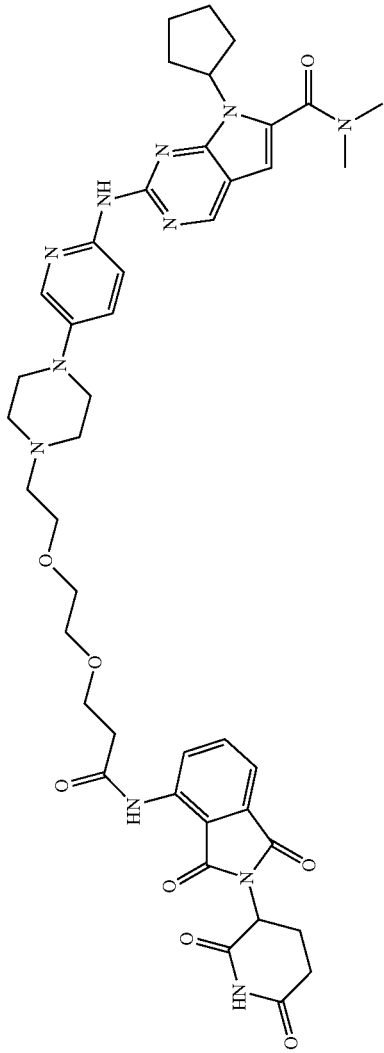 |
| 55 | 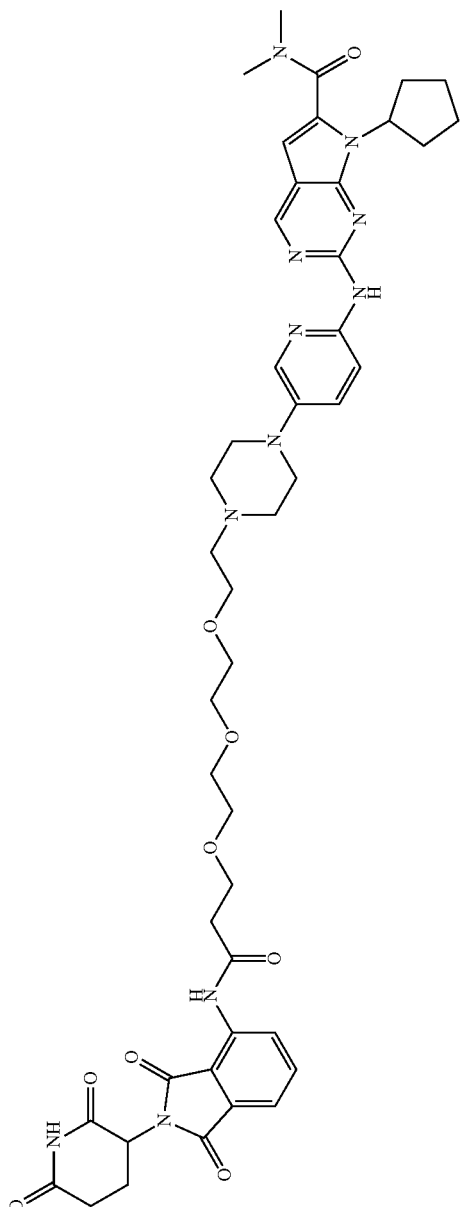 |

| No. | Structure |
|---|---|
| 56 | 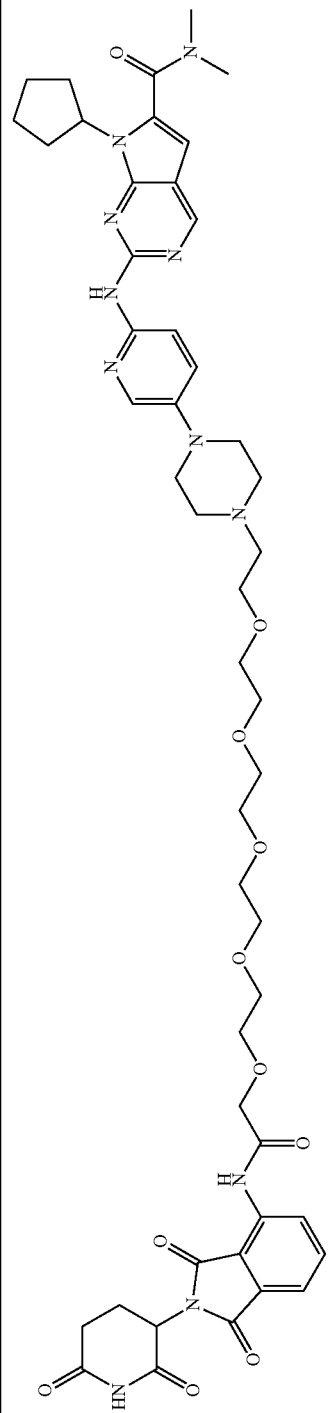 |
| 57 | 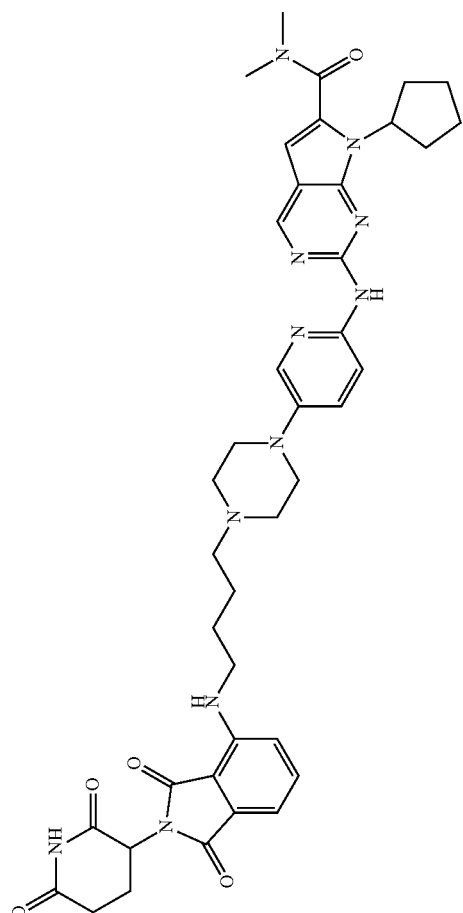 |

-continued
| No. | Structure |
|---|---|
| 58 | 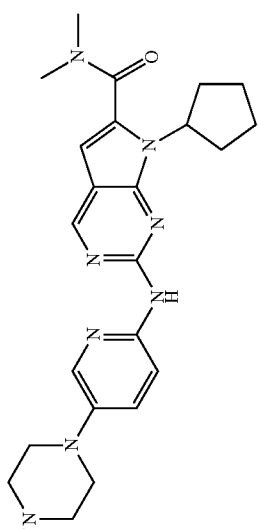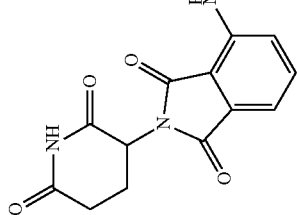 |
| 59 | 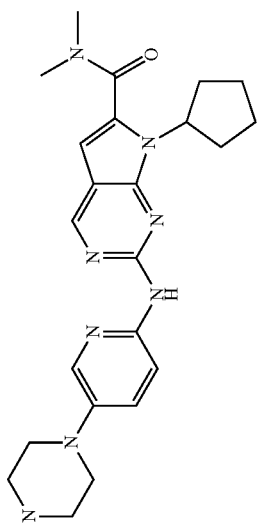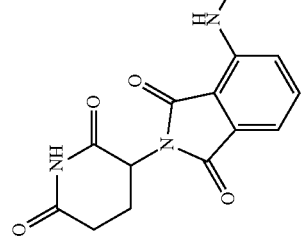 |

-continued
| No. | Structure |
|---|---|
| 60 | 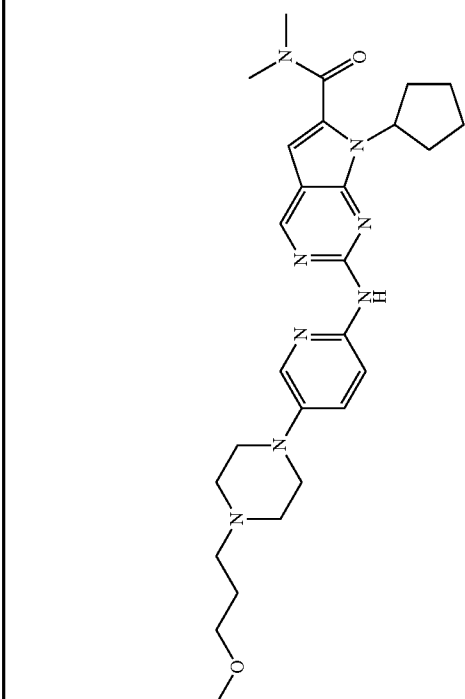 |
| 61 | 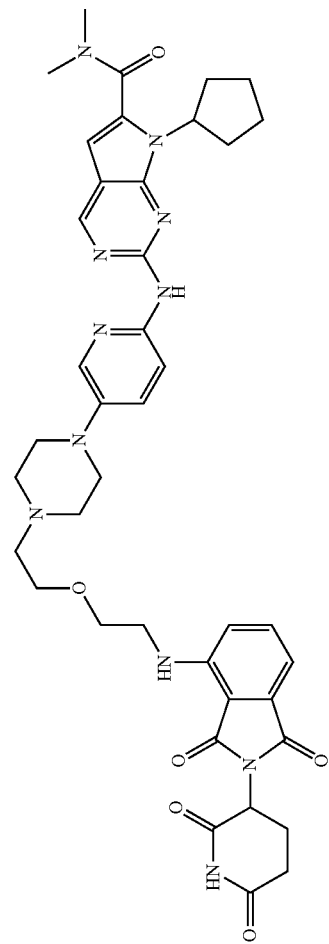 |

| No. | Structure |
|---|---|
| 62 | 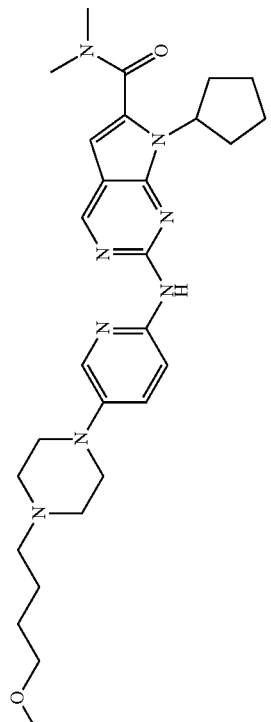 |
| 63 | 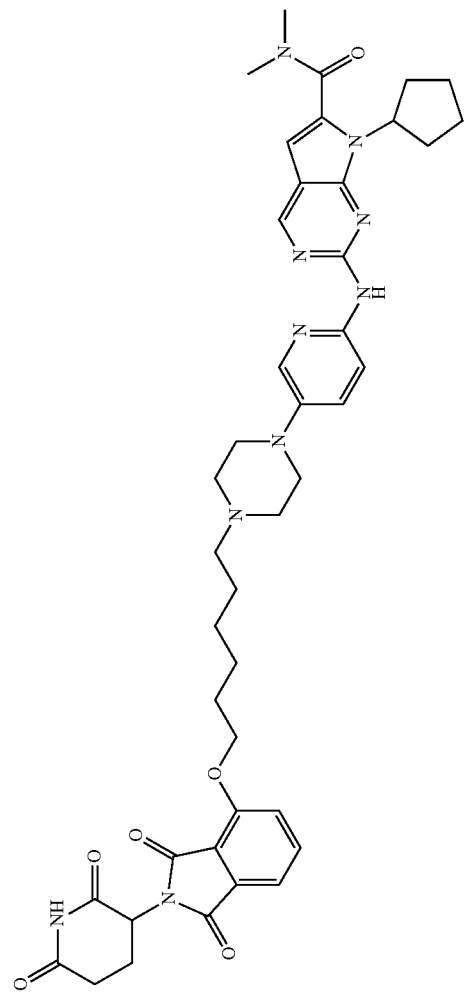 |

| No. | Structure |
|---|---|
| 64 | 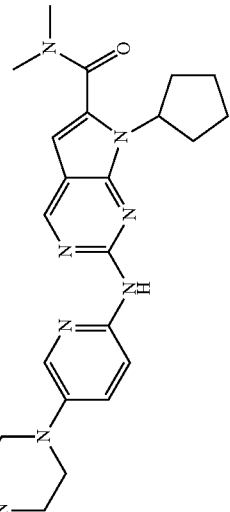 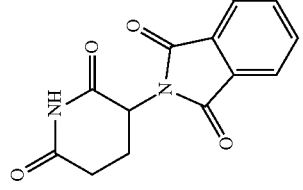 |
| 65 | 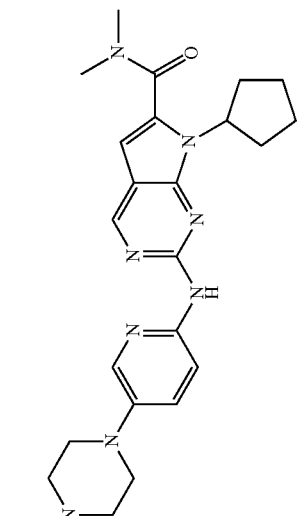 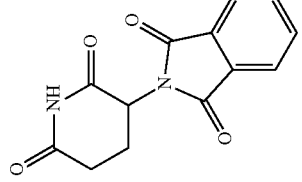 |

-continued
| No. | Structure |
|---|---|
| 66 | 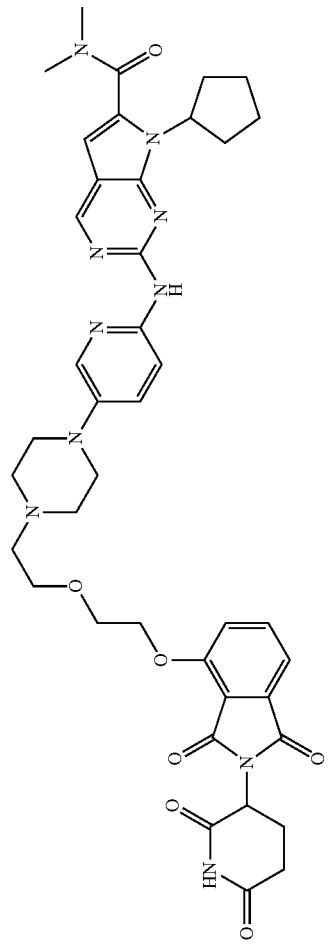 |

The compound of the present invention may form a pharmaceutically acceptable salt with an inorganic acid, an organic acid or a base. The inorganic acid includes, but is not limited to, hydrochloric acid, hydrobromic acid, nitric acid, perchloric acid, sulfuric acid, phosphoric acid and the like; the organic acid includes, but is not limited to, methanesulfonic acid, trifluoromethanesulfonic acid, ethanesulfonic acid, benzenesulfonic acid, p-toluenesulfonic acid, fumaric acid, oxalic acid, acetic acid, maleic acid, ascorbic acid, lactic acid, tartaric acid, malonic acid, glycolic acid, succinic acid, propionic acid and the like; the base includes, but is not limited to, an inorganic salt and an amine. The term of a pharmaceutically acceptable salt refers to those salts which, according to medical judgment, are suitable for use in contact with human and mammalian tissues without excessive toxicity, irritation, allergic reactions, and the like. Pharmaceutically acceptable salts are well known in the art. The present invention also encompasses pharmaceutical compositions containing a prodrug of a compound of formula I. Prodrugs include such compounds in which the precursor molecule is covalently bonded to the free carboxyl, hydroxyl, amino group of the compound of formula I via a carbonate bond, a urethane bond, an amide bond, an alkyl ester bond, a phosphate bond, or a phosphoramidate bond.

Preparation of Compound

Preparation Method

The method for preparing the compound of formula I according to the present invention is described in more detail below, but these specific methods do not constitute any limitation to the present invention. The compound of the present invention can also be conveniently prepared by combining various synthetic methods described in the specification or known in the art, and such combination can be easily performed by those skilled in the art to which the present invention belongs. The following reaction schemes illustrate the preparation of compounds of the present invention. Unless otherwise indicated, A, B, W, Y, Z, X, X', X", a, b, c, d, e, $R_1$, $R_2$, $R_3$, $R_4$, $R_5$, $R_6$, $R_7$, $R_8$, $R_9$, $R_{10}$ in the reaction scheme and subsequent discussions are as defined above, and $M_1$ and $M_2$ are leaving groups. In a preferred embodiment of the present invention, the method for preparing a compound of formula I provided by the present invention includes the steps:

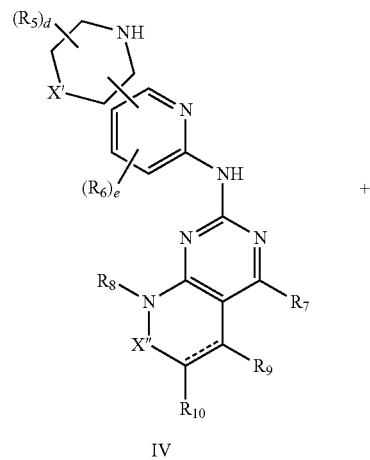

IV

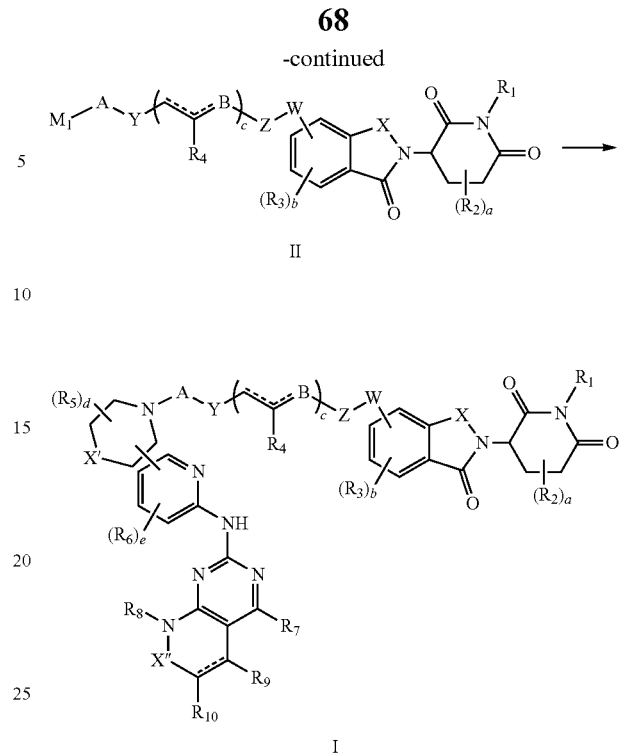

II

I (a) reacting a compound of formula IV and a compound of formula II in an inert solvent to obtain a compound of formula I; in the above formulas, the definition of each group is as described above, and $M_1$ is a leaving group. In another preferred example, the method further includes the step of:

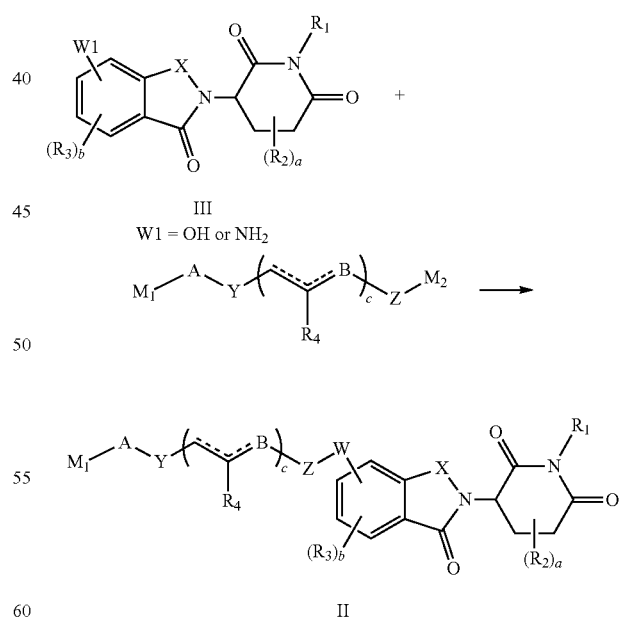

III
W1 = OH or NH2

II (b) reacting a compound of formula III and a compound of formula V in an inert solvent to obtain a compound of formula II; wherein $M_1$ and $M_2$ are leaving groups. In general, compounds of formula I can be obtained from those of formula III as described in the following

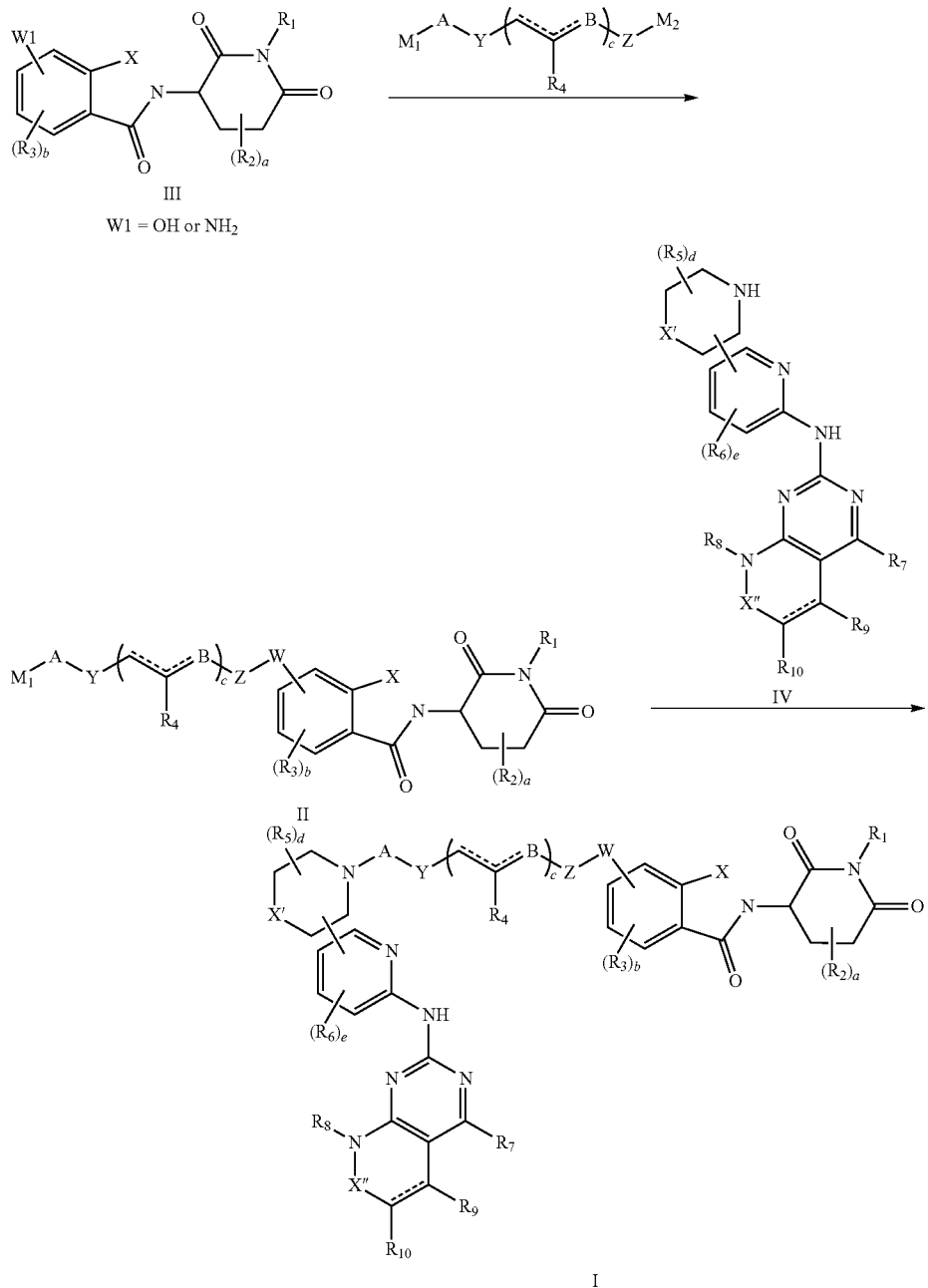

schemes:

In compound II, when W is an ether, it can be prepared by directly nucleophilic substitution of formula III (W1=OH) with an intermediate containing a leaving group under the action of a base, or by a photo-extension reaction with an alcohol; when W is an ester or carbamate (NHCO$_2$), it can be prepared by reacting formula III (W1=OH) with an acyl chloride, an activated ester (amide), a carboxylic acid, or an isocyanate under the action of a base; when W is an amine, it can be prepared by directly nucleophilic substitution of formula III (W1=NH$_2$) with an intermediate containing a leaving group under the action of a base, or by reductive amination reaction of formula III (W1=NH$_2$) with an aldehyde/ketone; when W it is an amide, alkoxycarbonylamine (OCONH) or urea, it can be prepared by reacting formula III (W1=NH$_2$) with the corresponding acyl chloride, activated ester (amide), carboxylic acid and isocyanate under the action of a base. In compound I, when A and a nitrogen atom are connected through a C—N bond, it can be prepared by direct substitution reaction or reductive amination reaction; when A and a nitrogen atom are connected in the form of amide, urea, carbamate, sulfonamide, or sulfamide, it can be prepared by using the corresponding acyl chloride, activated ester (amide), carboxylic acid, isocyanate, sulfonyl chloride, or sulfuryl chloride. Generally, according to the connection structure of A and W, compound I can also be obtained by first connecting formula IV to the middle chain and then reacting with formula III. The chemical synthesis method used is the same as described above. Compounds of formula III or IV can be obtained by known synthetic methods or can be easily obtained commercially.

Use of Compounds of Formula I

The compound of formula I can be used for one or more of the following purposes:

(a) preparation of drugs for the treatment of diseases related to the activity or expression level of cyclin-dependent kinase CDK; (b) preparation of cyclin-dependent kinase CDK targeting inhibitor or degradation agent; (c) non-therapeutic inhibition or degradation of cyclin-dependent kinase CDK in vitro; (d) non-therapeutic inhibition of cell proliferation in vitro; and/or (e) treatment of diseases related to the activity or expression level of cyclin-dependent kinase CDK. In another preferred example, the disease related to the activity or expression level of cyclin-dependent kinase CDK is a tumor or an autoimmune disease. The compound of formula I of the present invention can be used to prepare a pharmaceutical composition, which comprises: (i) an effective amount of a compound of formula I, or a pharmaceutically acceptable salt thereof; and (ii) a pharmaceutically acceptable carrier. In another preferred example, the effective amount refers to a therapeutically effective amount or an inhibitory effective amount. The compound of formula I of the present invention can also be used in a method for inhibiting or degrading cyclin-dependent kinase CDK, and the inhibition is a non-therapeutic inhibition in vitro or a therapeutic inhibition. In another preferred example, when an inhibitory effective amount of the compound of formula I of the present invention or a pharmaceutically acceptable salt thereof is administered to an inhibitory subject, the inhibitory effective amount is 0.001-500 nmol/L, preferably 0.01-200 nmol/L. In particular, the present invention also provides a method of treating a disease related to the activity or expression level of cyclin-dependent kinase CDK, and the method comprises: administering a therapeutically effective amount of a compound of formula I or a pharmaceutical composition containing the compound of formula I as an active ingredient to a treating subject.

Pharmaceutical Composition and Administration

Since the compound of the present invention has excellent inhibitory activity on cyclin-dependent kinase CDK, the compound of the present invention and its various crystal forms, pharmaceutically acceptable inorganic or organic salts, hydrates or solvates and the pharmaceutical composition containing the compound of the present invention as a main active ingredient can be used for treating, preventing, and alleviating diseases related to CDK activity or expression level. According to the prior art, the compounds of the present invention are useful for treating diseases including tumors and the like. The pharmaceutical composition of the present invention comprises the compound of the present invention or the pharmaceutically acceptable salt thereof in a safe and effective amount range and pharmaceutically acceptable excipients or carriers. The "safe and effective amount" means: the amount of the compound is sufficient to significantly improve the condition, but will not have serious side effects. Generally, the pharmaceutical composition contains 1-2000 mg of the compound of the present invention per dose, preferably, 5-200 mg the compound of the present invention per dose. Preferably, "one dose" is a capsule or tablet." Pharmaceutically acceptable carrier" means one or more compatible solid or liquid fillers or gelatinous materials which are suitable for human use and should be of sufficient purity and sufficiently low toxicity. "Compatible" herein means that each component in the composition can be well blended with a compound of the present invention and with each other between them, without significantly reducing the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc. There is no special limitation of administration mode for the compound or pharmaceutical compositions of the present invention, and the representative administration mode includes (but is not limited to): oral, intratumoral, rectal, parenteral (intravenous, intramuscular or subcutaneous), and topical administration. Solid dosage forms for oral administration include capsules, tablets, pills, powders and granules. In these solid dosage forms, the active compounds are mixed with at least one conventional inert excipient (or carrier), such as sodium citrate or dicalcium phosphate, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent and the release of the active compounds or compounds in the compositions can be released in a delayed mode in a given portion of the digestive tract. Examples of the embedding components include polymers and waxes. If necessary, the active compounds and one or more above excipients can form microcapsules. Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof. Besides these inert diluents, the composition may also contain additives such as wetting agents, emulsifiers and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof. The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof. The dosage forms for topical administration of compounds of the present invention include ointments, powders, patches, aerosol, and inhalants. The active ingredients are mixed with physiologically acceptable carriers and any preservatives, buffers, or propellant if necessary, under sterile conditions.

Compounds of the present invention can be administered alone, or in combination with any other pharmaceutically acceptable compounds. When the pharmaceutical compositions are used, a safe and effective amount of compound of the present invention is applied to a mammal (such as human) in need of, in which the dose of administration is a pharmaceutically effective dose. For a person weighed 60 kg, the daily dose is usually 1-2000 mg, preferably 5-500 mg. Of course, the particular dose should also depend on various factors, such as the route of administration, the healthy condition of patient, which are well within the skills of an experienced physician.

Main Advantages of the Invention

1. Compounds of formula I are provided.

2. A novel CDK inhibitor and degradation agent, the preparation thereof and the application thereof are provided. The inhibitor and degradation agent can inhibit the activity of CDK and degrade CDK at a very low concentration.

3. A pharmaceutical composition for treating diseases related to CDK activity is provided.

The present invention will be further illustrated below with reference to the specific examples. It should be understood that these examples are only to illustrate the invention but not to limit the disclosure of the invention. The experimental methods without specific conditions in the following embodiments are generally carried out according to conventional conditions, or in accordance with the conditions recommended by the manufacturer. Unless stated otherwise, percentages and parts are percentages by weight and parts by weight.

Example 1: Preparation of Compound 3

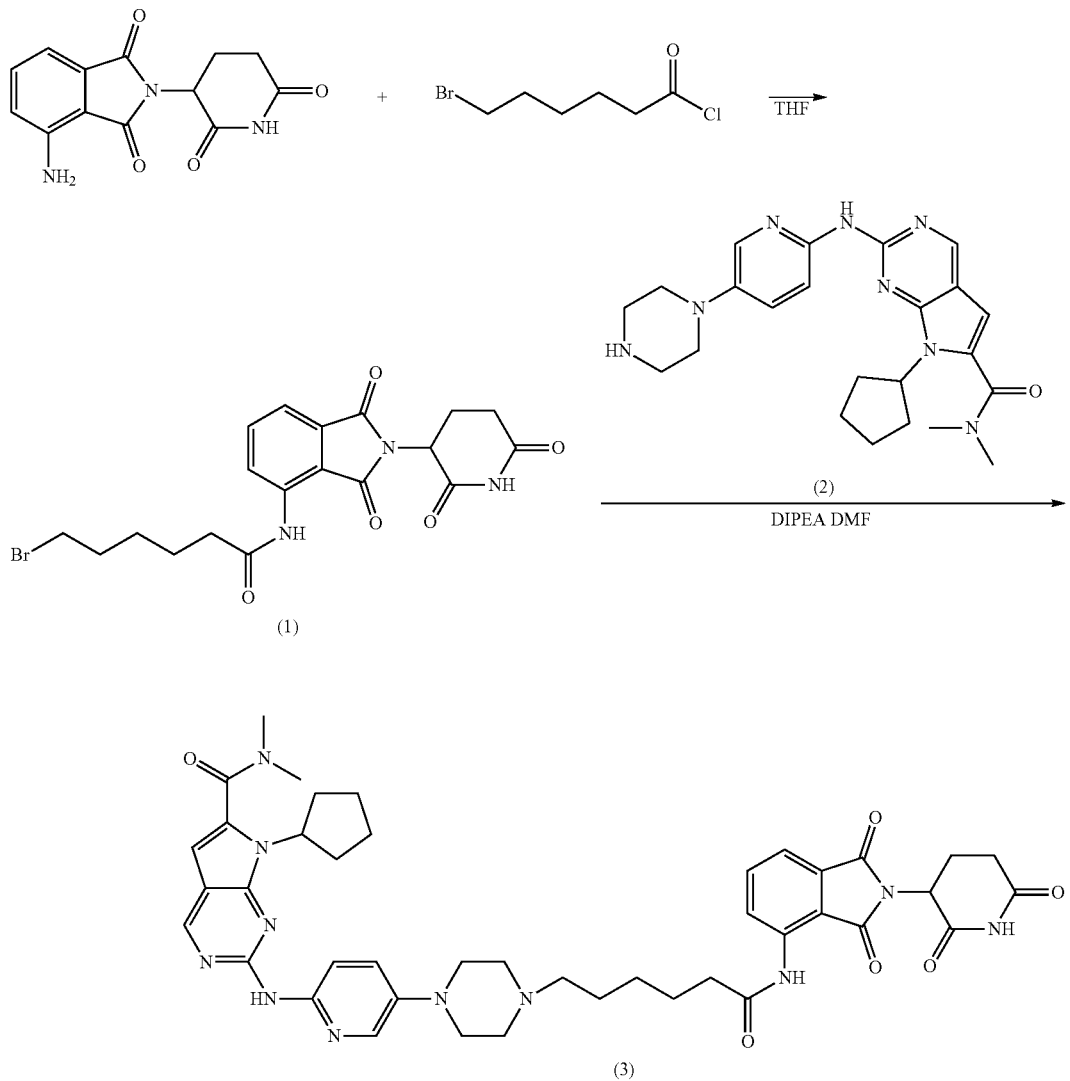

Step 1: 2.14 g of 6-bromohexanoyl chloride and 1.37 g of pomalidomide were dissolved in 50 ml of THF, and the mixture was stirred at reflux for 8 h. Then the solvent was removed under reduced pressure and the residue was purified by column chromatography to obtain 1.22 g of compound (1). MS (ESI): 450 [M+H]+.

Step 2: 1.00 g of compound (1), 1.19 g of compound (2) and 0.57 g of diisopropylethylamine were dissolved in 30 ml of DMF. The mixture was stirred at 80° C. for 6 h, and then cooled to room temperature. After concentration, the residue was purified by column chromatography to obtain 1.21 g of compound (3) with a yield of 66.7%. MS (ESI): 804 [M+H]+. 1H NMR (400 MHz, CDCl3) δ: 9.79 (br, 1H), 8.70 (s, 1H), 8.34 (d, J=9.2 Hz, 1H), 8.24 (s, 1H), 8.03 (d, J=3.2 Hz, 1H), 7.49 (dd, J=8.4, 7.6 Hz, 1H), 7.33 (dd, J=9.6, 3.2 Hz, 1H), 7.11 (d, J=6.8 Hz, 1H), 6.91 (d, J=8.4 Hz, 1H), 6.52 (t, J=5.6 Hz, 1H), 6.43 (s, 1H), 4.90 (dd, J=12.0, 5.6 Hz, 1H), 4.78 (m, 1H), 3.64-3.76 (m, 4H), 3.15 (s, 6H), 2.53-2.90 (m, 6H), 2.39 (t, J=7.2 Hz, 2H), 1.35-2.16 (m, 18H).

Example 2: Preparation of Compound 8

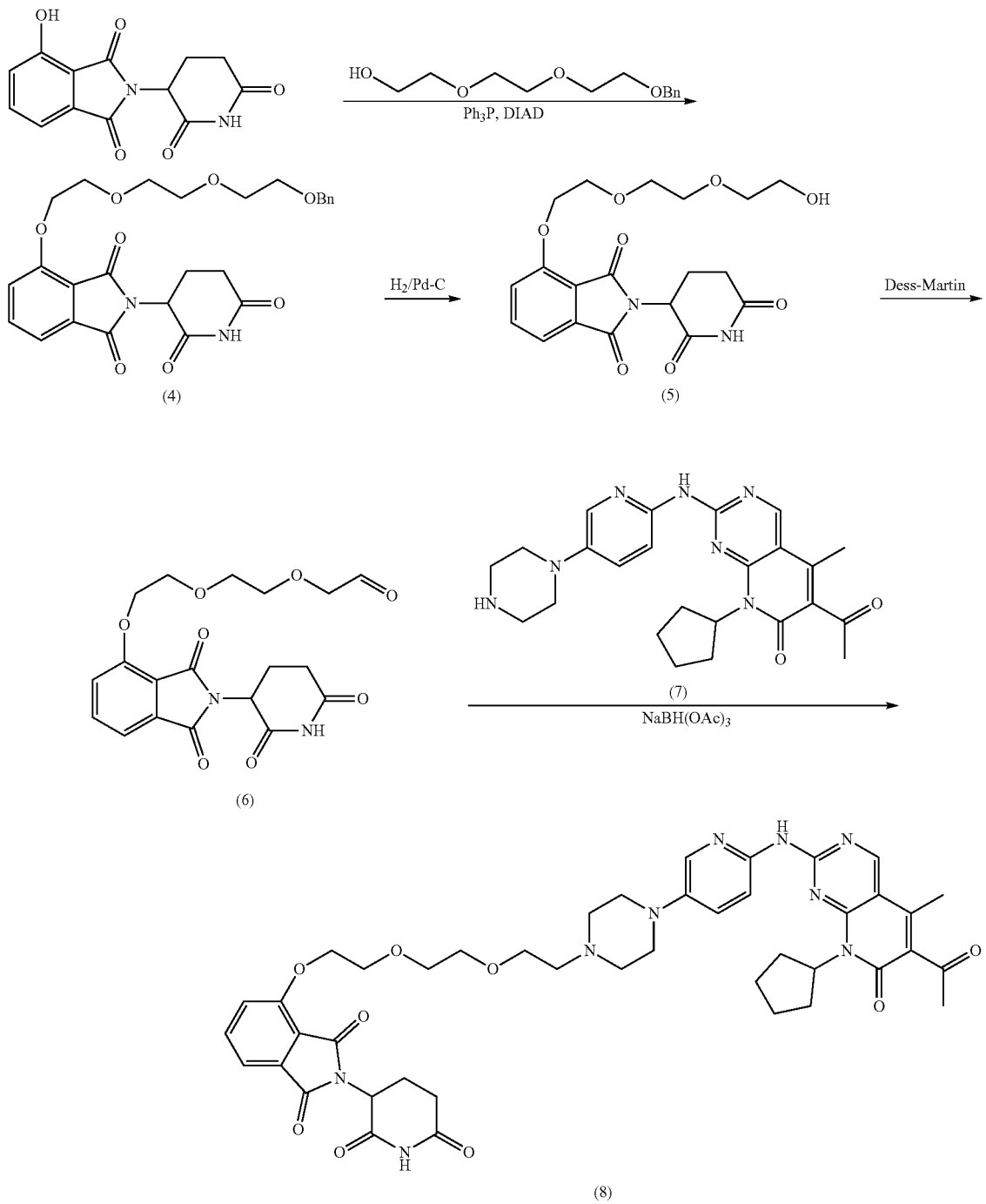

Step 1: 100 mg of 4-hydroxythalidomide, 96 mg of triethylene glycol monobenzyl ether, and 100 mg of triphenylphosphine were dissolved in 10 ml of anhydrous THF, and then 95 mg of DIAD was added dropwise. The reaction was carried out at room temperature for 2 h. THF was removed under reduced pressure, and 110 mg of compound (4) was obtained after purification by column chromatography. MS (ESI): 497 [M+H]+.

Step 2: 100 mg of compound (4) and 100 mg of 10% Pd—C were added into 10 ml of methanol and the mixture was hydrogenated at room temperature overnight. Then the mixture was filtered and the filtrate was concentrated. The residue was purified by column chromatography to obtain 40 mg of compound (5). MS (ESI): 407 [M+H]+.

Step 3: 30 mg of compound (5) was dissolved in 5 ml of DCM, and then 47 mg of Dess-martin oxidant was added. The mixture was reacted at room temperature for 3 h. To the reaction system were added a saturated aqueous solution of NaHCO₃ and a saturated aqueous solution of Na₂S₂O₃, and stirred for 5 min. The organic layer was separated, dried over anhydrous Na₂S₂O₃, and concentrated to dryness. The obtained compound (6) was directly used in the next step.

After compound (6) was dissolved in 5 ml of DCM, 50 mg of raw material (7) and 30 mg of NaBH(OAc)₃ were added, and the mixture was reacted overnight at room temperature. DCM was distilled off under reduced pressure. 30 mg of compound (8) was obtained after purification by column chromatography. MS (ESI): 836 [M+H]+. 1H NMR (400 MHz, CDCl3) δ: 9.85 (br, 1H), 8.83 (s, 1H), 8.75 (br, 1H), 8.15 (d, J=8.8 Hz, 1H), 8.07 (d, J=2.8 Hz, 1H), 7.67 (dd, J=8.4, 7.6 Hz, 1H), 7.47 (d, J=6.8 Hz, 1H), 7.32 (dd, J=8.8, 2.8 Hz 1H), 7.26 (d, J=8.4 Hz, 1H), 5.87 (m, 1H), 4.95 (dd, J=12.0, 5.2 Hz, 1H), 4.35 (t, J=4.8 Hz, 2H), 3.95 (t, J=4.8 Hz, 2H), 3.80 (m, 2H), 3.66 (m, 4H), 3.22 (m, 4H), 2.68-2.92 (m, 8H), 2.55 (s, 3H), 2.48-2.65 (m, 1H), 2.37 (s, 3H), 2.30-2.41 (m, 2H), 2.00-2.16 (m, 3H), 1.86 (br, 2H), 1.67 (m, 2H).

Example 3: Preparation of Compound 11

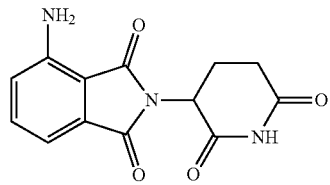 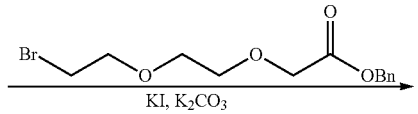

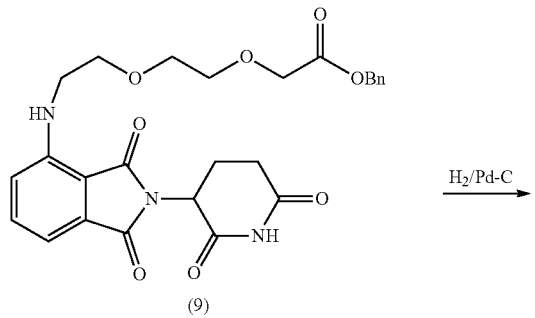

(9)

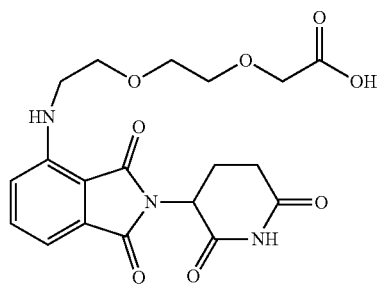 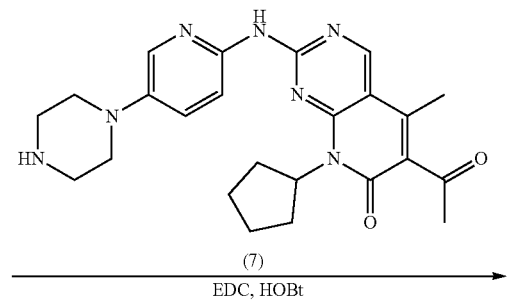

(10)

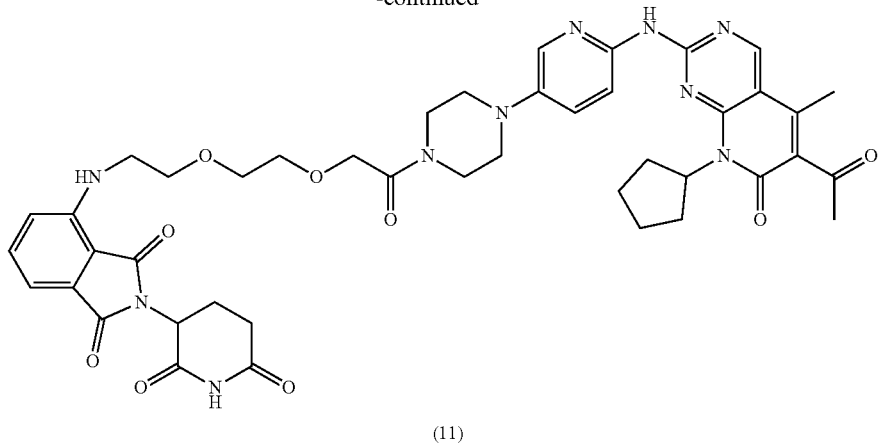

(11)

Step 1: 174 mg of benzyl 2-(2-(2-bromoethoxy)ethoxy) acetate, 100 mg of potassium carbonate, 20 mg of potassium iodide and 100 mg of pomalidomide were added into 20 ml of DMF (N, N-dimethylformamide), and reacted at 80° C. overnight. The reaction solution was purified by column chromatography to obtain 113 mg of compound (9). MS (ESI): 510 [M+H]$^+$.

Step 2: 100 mg of compound (9) and 100 mg of 10% Pd—C were added into 10 ml of methanol and the mixture was hydrogenated at room temperature overnight. Then the mixture was filtered and the filtrate was concentrated. The residue was purified by column chromatography to obtain 73 mg of compound (10). MS (ESI anion): 418 [M−H]$^-$.

Step 3: 50 mg of compound (10) and 50 mg of raw material (7) were dissolved in 5 ml of dichloromethane, and 20 mg of HOBt (1-hydroxybenzotriazole) and 40 mg of EDC (1-(3-dimethylaminopropyl)-3-ethyl-carbodiimide hydrochloride) were added. The mixture was reacted at room temperature overnight. Dichloromethane was distilled off under reduced pressure, and 32 mg of compound (11) was obtained after purification by column chromatography. MS (ESI): 849 [M+H]$^+$. 1H NMR (400 MHz, CDCl3) δ 9.73 (br, 1H), 8.82 (s, 1H), 8.52 (br, 1H), 8.14 (d, J=9.2 Hz, 1H), 8.08 (d, J=2.8 Hz, 1H), 7.49 (dd, J=8.4, 7.2 Hz, 1H), 7.33 (dd, J=9.2, 2.8 Hz, 1H), 7.11 (d, J=7.2 Hz, 1H), 6.91 (d, J=8.4 Hz, 1H), 6.52 (t, J=5.6 Hz, 1H), 5.87 (m, 1H), 4.90 (dd, J=12.0, 5.2 Hz, 1H), 4.53 (br, 2H), 3.58-3.76 (m, 10H), 3.48 (dd, J=11.2, 5.6 Hz, 2H), 3.22 (t, J=4.8 Hz, 4H), 2.65-2.91 (m, 4H), 2.55 (s, 3H), 2.37 (s, 3H), 2.30-2.39 (m, 2H), 2.00-2.16 (m, 2H), 1.62-1.92 (m 4H).

Example 4: Preparation of Compound 14

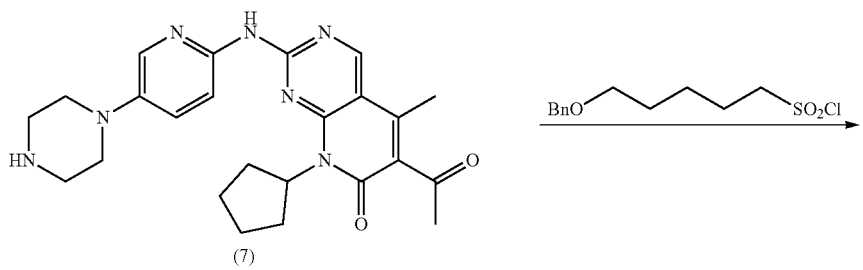

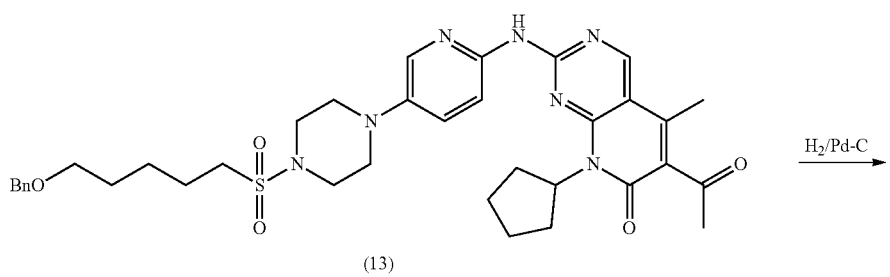

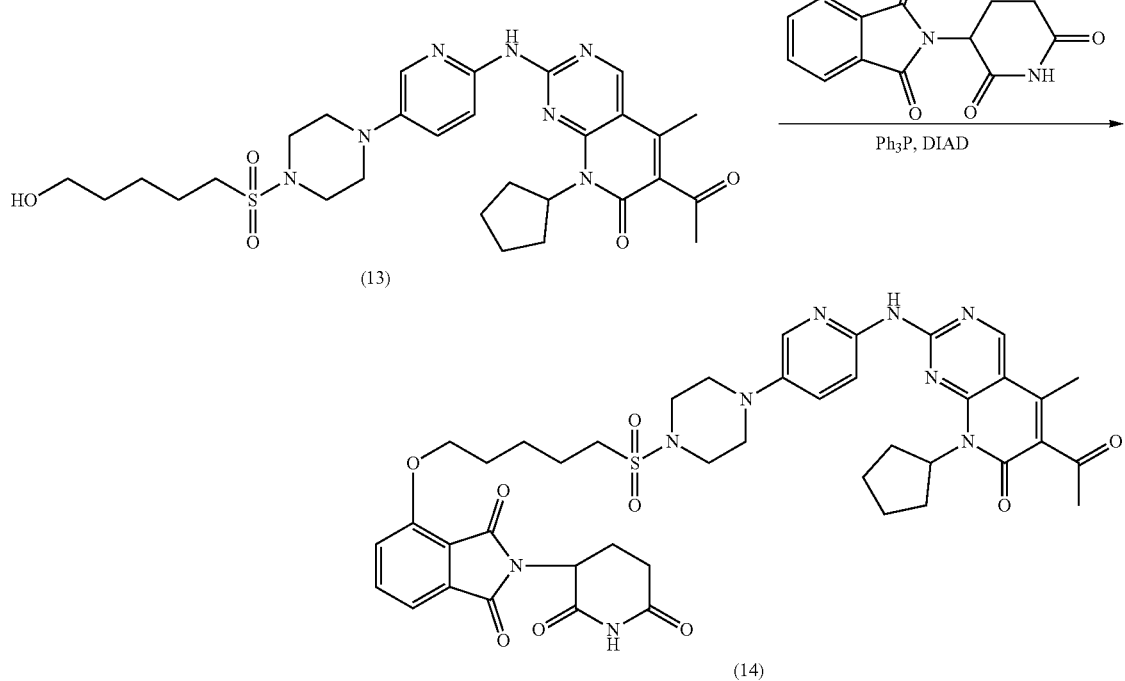

Step 1:

200 mg of the raw material (7) was dissolved in 20 ml of dichloromethane, 100 mg of triethylamine and 135 mg of 5-benzyloxypentanesulfonyl chloride were added, and the mixture was reacted at room temperature overnight. The solvent was removed under reduced pressure, and 254 mg of compound (12) was obtained after purification by column chromatography. MS (ESI): 688 [M+H]⁺.

Step 2:

200 mg of compound (12) and 200 mg of 10% Pd—C were added into 20 ml of methanol and the mixture was hydrogenated at room temperature overnight. Then the mixture was filtered and the filtrate was concentrated. The residue was purified by column chromatography to obtain 161 mg of compound (13). MS (ESI): 598 [M+H]⁺.

Step 3:

50 mg of 4-hydroxythalidomide, 50 mg of triphenylphosphine and 80 mg of compound (13) were dissolved in 5 ml of anhydrous tetrahydrofuran, 50 mg of DIAD (diisopropyl azodicarboxylate) was added dropwise, and the reaction was carried out at room temperature for 3 h. Tetrahydrofuran was removed under reduced pressure, and 36 mg of compound (14) was obtained after purification by column chromatography. MS (ESI): 854 [M+H]⁺. 1H NMR (400 MHz, CDCl3) δ 9.92 (br, 1H), 8.83 (s, 1H), 8.75 (br, 1H), 8.16 (d, J=8.4 Hz, 1H), 8.08 (d, J=2.8 Hz, 1H), 7.67 (dd, J=8.4, 7.6 Hz, 1H), 7.49 (d, J=7.2 Hz, 1H), 7.33 (dd, J=8.4, 2.8 Hz 1H), 7.25 (d, J=8.4 Hz, 1H), 5.82 (m, 1H), 4.93 (dd, J=12.0, 5.6 Hz, 1H), 3.95 (t, J=7.2 Hz, 2H), 3.78 (t, J=6.8 Hz, 2H), 3.50-3.68 (m, 4H), 2.55 (s, 3H), 2.37 (s, 3H), 2.32-2.73 (m, 4H), 2.00-2.26 (m, 10H), 1.34-1.92 (m, 8H).

Similarly, the following compounds were prepared by a method similar to the above example:

| Compound No. | Structure of compound | Reference example for synthesis | MS(ESI) |
|---|---|---|---|
| 15 | | 2, 3 | 835[M + H]$^+$ |
| 16 | | 2, 3 | 879[M + H]$^+$ |

| Compound No. | Structure of compound | Reference example for synthesis | MS(ESI) |
|---|---|---|---|
| 17 | 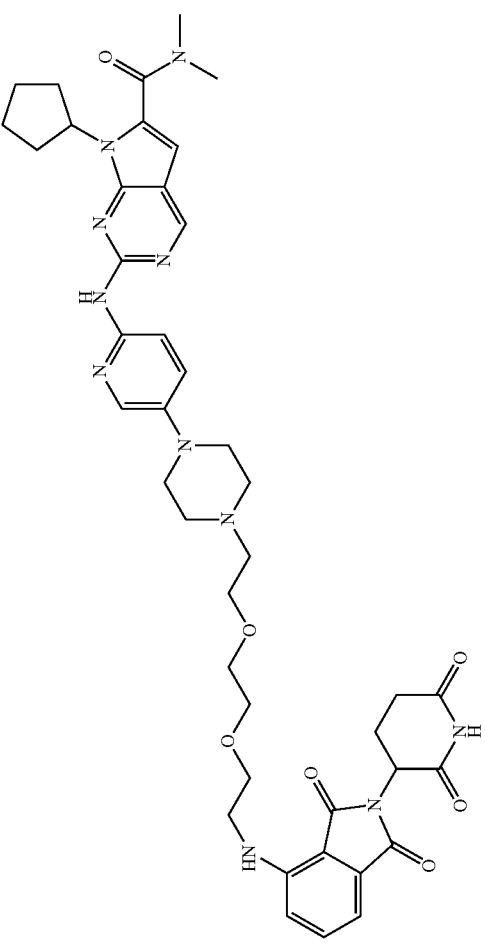 | 2, 3 | 822[M + H]+ |
| 18 | 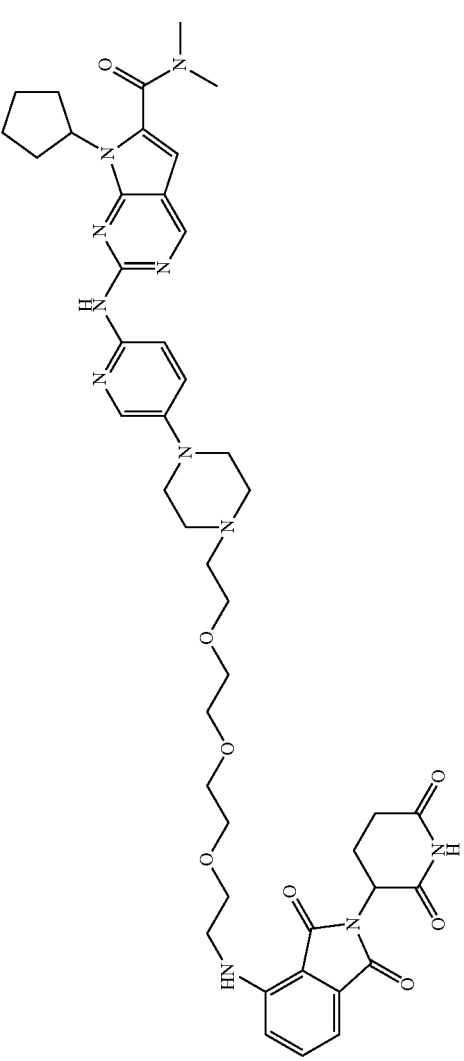 | 2, 3 | 867[M + H]+ |

-continued

| Compound No. | Structure of compound | Reference example for synthesis | MS(ESI) |
|---|---|---|---|
| 19 | | 2 | 823[M + H]+ |
| 20 | | 2 | 867[M + H]+ |

| Compound No. | Structure of compound | Reference example for synthesis | MS(ESI) |
|---|---|---|---|
| 21 | | 2 | 880[M + H]+ |
| 23 | | 2 | 804[M + H]+ |
| 24 | | 2 | 776[M + H]+ |

| Compound No. | Structure of compound | Reference example for synthesis | MS(ESI) |
|---|---|---|---|
| 25 | 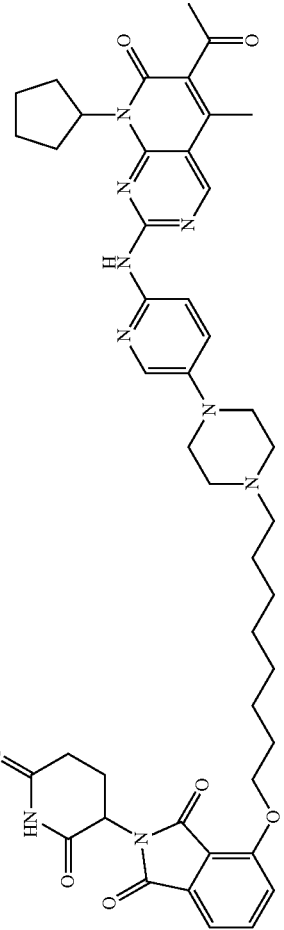 | 2 | 832[M + H]+ |
| 26 | 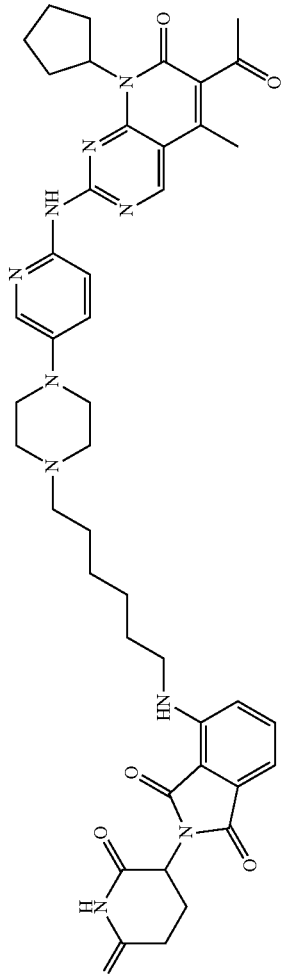 | 2, 3 | 803[M + H]+ |
| 27 | 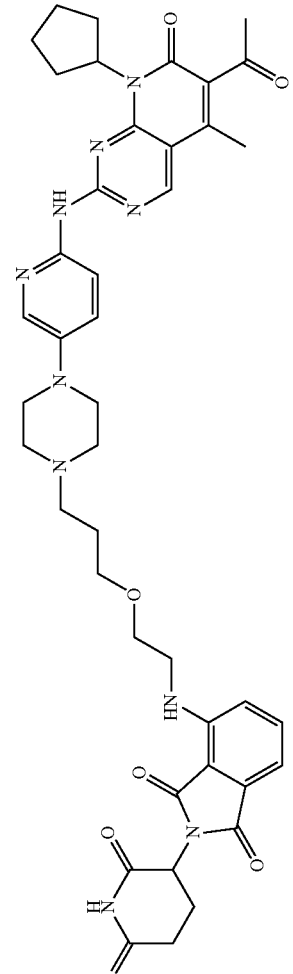 | 2, 3 | 805[M + H]+ |

-continued

| Compound No. | Structure of compound | Reference example for synthesis | MS(ESI) |
|---|---|---|---|
| 28 | | 2, 3 | 805[M + H]+ |
| 29 | | 2, 3 | 791[M + H]+ |

| Compound No. | Structure of compound | Reference example for synthesis | MS(ESI) |
|---|---|---|---|
| 30 | | 2 | 806[M + H]+ |
| 31 | | 2 | 806[M + H]+ |

-continued
| Compound No. | Structure of compound | Reference example for synthesis | MS(ESI) |
|---|---|---|---|
| 32 | 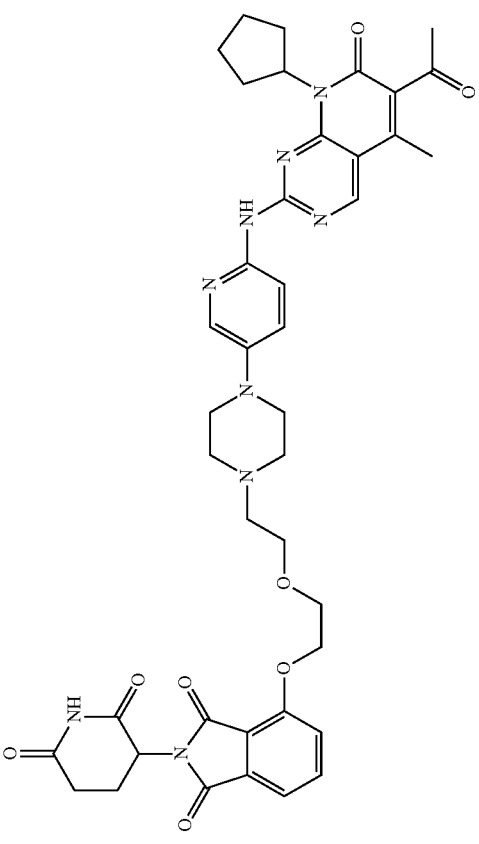 | 2 | 792[M + H]+ |

-continued
| Compound No. | Structure of compound | Reference example for synthesis | MS(ESI) |
|---|---|---|---|
| 33 | 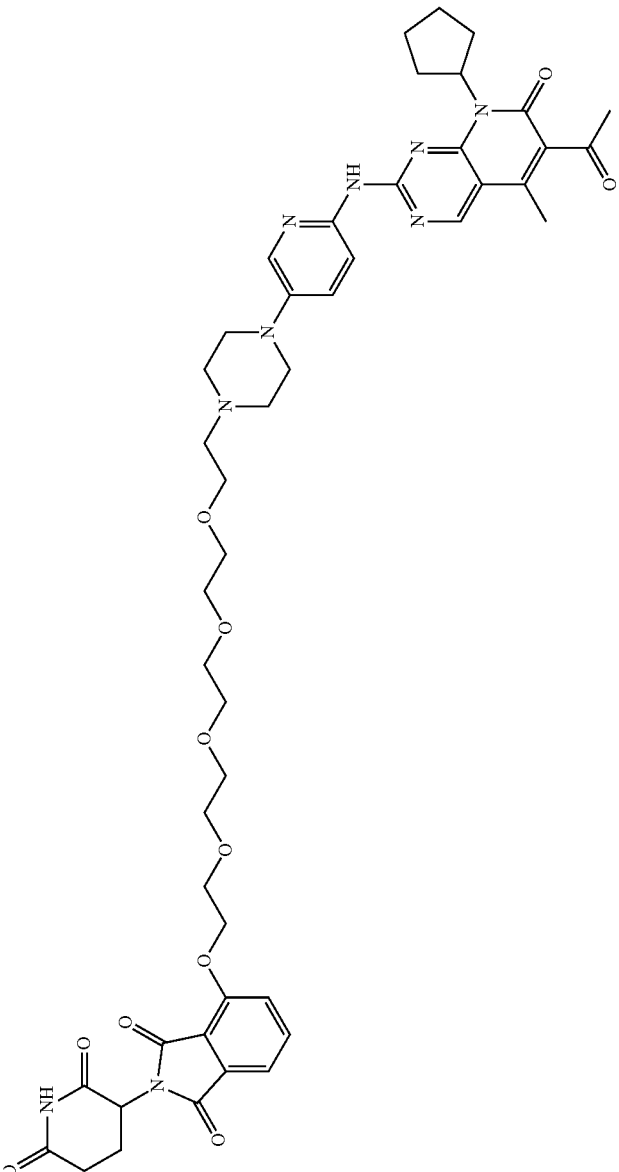 | 2 | 924[M + H]+ |

-continued

| Compound No. | Structure of compound | Reference example for synthesis | MS(ESI) [M + H]+ |
|---|---|---|---|
| 34 | | 2, 3 | 923[M + H]+ |
| 35 | | 1 | 819[M + H]+ |

-continued

| Compound No. | Structure of compound | Reference example for synthesis | MS(ESI) |
|---|---|---|---|
| 36 | | 1 | 863[M + H]+ |
| 37 | | 1 | 907[M + H]+ |

| Compound No. | Structure of compound | Reference example for synthesis | MS(ESI) |
|---|---|---|---|
| 38 | | 2 | 847[M + H]+ |
| 39 | | 2 | 849[M + H]+ |

-continued

| Compound No. | Structure of compound | Reference example for synthesis | MS(ESI) |
|---|---|---|---|
| 40 | | 2 | 893[M + H]+ |
| 41 | | 2 | 937[M + H]+ |

-continued

| Compound No. | Structure of compound | Reference example for synthesis | MS(ESI) |
|---|---|---|---|
| 42 | | 2, 3 | 910[M + H]+ |
| 43 | | 2, 3 | 954[M + H]+ |

-continued

| Compound No. | Structure of compound | Reference example for synthesis | MS(ESI) |
|---|---|---|---|
| 44 | | 2 | 911[M + H]+ |
| 45 | | 2 | 955[M + H]+ |

-continued

| Compound No. | Structure of compound | Reference example for synthesis | MS(ESI) |
|---|---|---|---|
| 46 | | 2 | 806[M + H]+ |
| 47 | | 2 | 834[M + H]+ |

| Compound No. | Structure of compound | Reference example for synthesis | MS(ESI) |
| --- | --- | --- | --- |
| 48 | | 2 | 836[M + H]+ |
| 49 | | 2 | 880[M + H]+ |

-continued

| Compound No. | Structure of compound | Reference example for synthesis | MS(ESI) |
|---|---|---|---|
| 50 | | 2 | 924[M + H]+ |
| 51 | | 2 | 968[M + H]+ |

-continued

| Compound No. | Structure of compound | Reference example for synthesis | MS(ESI) |
|---|---|---|---|
| 52 | | 1 | 776[M + H]+ |
| 53 | | 1 | 806[M + H]+ |

-continued

| Compound No. | Structure of compound | Reference example for synthesis | MS(ESI) |
|---|---|---|---|
| 54 | | 1 | 850[M + H]+ |
| 55 | | 1 | 894[M + H]+ |

-continued
| Compound No. | Structure of compound | Reference example for synthesis | MS(ESI) MS[M + H]+ |
|---|---|---|---|
| 56 | 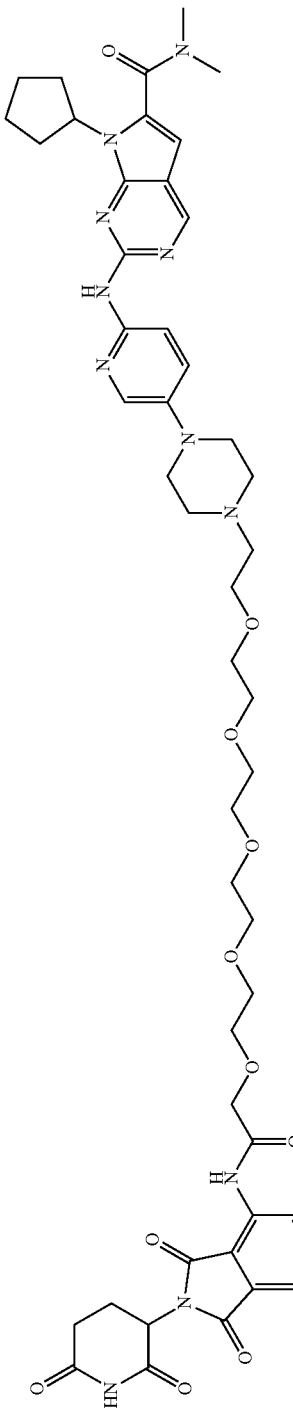 | 1 | 968[M + H]+ |
| 57 | 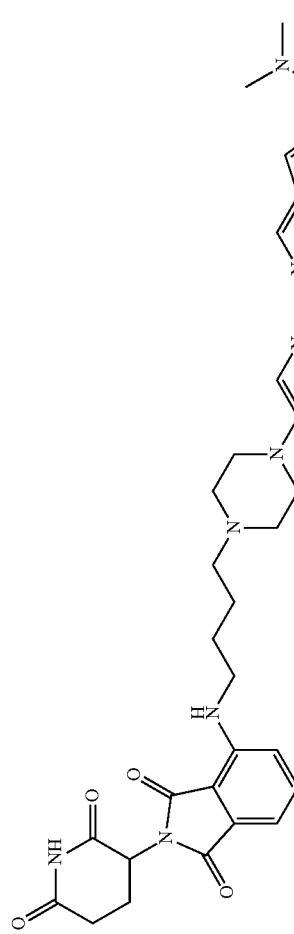 | 2, 3 | 762[M + H]+ |

-continued

| Compound No. | Structure of compound | Reference example for synthesis | MS(ESI) |
|---|---|---|---|
| 58 | | 2, 3 | 790[M + H]+ |
| 59 | | 2, 3 | 818[M + H]+ |

-continued

| Compound No. | Structure of compound | Reference example for synthesis | MS(ESI) |
|---|---|---|---|
| 60 | | 2, 3 | 792[M + H]+ |
| 61 | | 2, 3 | 778[M + H]+ |

| Compound No. | Structure of compound | Reference example for synthesis | MS(ESI) |
|---|---|---|---|
| 62 | | 2 | 763[M + H]+ |
| 63 | | 2 | 791[M + H]+ |

-continued

| Compound No. | Structure of compound | Reference example for synthesis | MS(ESI) |
|---|---|---|---|
| 64 | | 2 | 819[M + H]+ |
| 65 | | 2 | 793[M + H]+ |

-continued

| Compound No. | Structure of compound | Reference example for synthesis | MS(ESI) |
|---|---|---|---|
| 66 | | 2 | 779[M + H]+ |

Example 5: Testing the CDK4/6 Inhibition of Compound by Caliper Assay

The experimental steps were as follows:

Preparation of 1×kinase reaction buffer (50 mM HEPES, PH 7.5; 0.0015% Brij-35) and kinase reaction termination solution (100 mM HEPES, PH 7.5; 0.0015% Brij-35; 0.2% Coating Reagent; 50 mM EDTA) preparation of experimental samples: 100 µL of 5 µM sample solution (dissolved in 100% DMSO) was added to a 96-well plate to obtain a 50×sample solution. As controls, two wells containing only 100 µL of 100% DMSO were set on the same plate. One was served as a control without samples and the other was served as a control without enzymes. 10 µL of sample and 90 µL of 1×kinase reaction buffer were added to a 96-well plate as a transfer plate. The transfer plate was shaken for 10 minutes.

Preparation of the test plate: taking 5 µL of each of the prepared samples in the 96-well transfer plate into a 384-well plate. Kinase reaction: to 5 µL of 5×compound solution (dissolved in DMSO, diluted 10 times with water) was added 10 µL of 2.5×CDK4/6 kinase solution (kinase was diluted with 1×kinase reaction buffer), which was incubated at room temperature for 10 min, and then 10 µL of 2.5× substrate peptide solution (FAM-labeled peptide and ATP were diluted with 1×kinase reaction buffer) was added. Termination of the kinase reaction: 25 µL of kinase reaction termination solution was added after being reacted at 28° C. for a period of time. The fluorescence (F) was tested on a Caliper and data was collected. The inhibition rate of kinase activity was calculated: the percent inhibition rate of kinase activity=$(F_{DMSO\ control}-F_{sample})/(F_{DMSO\ control}-F_{negative\ control})\times 100\%$, with DMSO as the solution control, and no kinase as the negative control. The results show that the inhibitory activity of compound (100 nM) on CDK4/6 is shown in the following table:

| Compound No. | Inhibition (%) (CDK4) | Inhibition (%) (CDK6) |
|---|---|---|
| 3 | 97 | 86 |
| 8 | 82 | 84 |
| 11 | 93 | 79 |
| 14 | 92 | 85 |
| 15 | 91 | 69 |
| 16 | 97 | 68 |
| 17 | 82 | 25 |
| 18 | 80 | 29 |
| 19 | 80 | 43 |
| 21 | 93 | 97 |
| 24 | 96 | 91 |

Example 6: Testing the CDK4/6 Protein Degradation Activity of Compounds by Western Blot Cell lines: MCF-7 cell lines (human breast cancer cells, available from ATCC) were cultured in MEM medium containing 10% calf serum in a 37° C., 5% $CO_2$, and saturated humidity incubator. DMSO control group and compound intervention group (1 µM) were set. Cells were collected after the treatment for 24 hours, then 100 µL of pre-chilled cell lysate was added and cells were lysed on ice for 30 minutes, total cell protein was extracted, and protein concentration was determined and quantified by bicinchoninic acid method. After routine gelatinization, loading, electrophoresis, then transferring to membrane and blocking, rabbit anti-human CDK4 (1:450) and rabbit anti-human CDK6 (1:150) were added and incubated at 4° C. overnight. The mixture was rinsed and then secondary antibody IgG (1:5000) was added. After the rinsing it was developed by the ECL developing solution, the Bio-Rad gel imaging system was used for scanning and imaging, and the computer software was used for analysis. Glycerol phosphate dehydrogenase (GAPDH) was used as an internal control. Image J software was used to analyze the gray scale of each band to calculate the degradation rate of the compound to degrade CDK4/6 protein. The degradation rate of CDK4/6 protein in MCF-7 cells by the compound is shown in the following table:

| Compound No. | Degradation activity (CDK4) | Degradation activity (CDK6) |
|---|---|---|
| 3 | ++++ | +++ |
| 8 | +++ | +++ |
| 21 | +++ | +++ |
| 16 | +++ | +++ |
| 17 | +++ | +++ |
| 18 | ++++ | ++++ |
| 19 | ++++ | +++ |
| 20 | +++ | +++ |
| 21 | +++ | +++ |
| 23 | +++ | +++ |
| 24 | ++++ | ++++ |
| 25 | +++ | +++ |
| 26 | +++ | +++ |
| 27 | +++ | +++ |
| 28 | +++ | +++ |
| 38 | ++++ | ++++ |
| 46 | ++++ | +++ |
| 47 | ++++ | +++ |
| 48 | ++++ | +++ |

Note:
In the above table, "−" represents no degradation activity, "+" represents a degradation rate of 10%-30%, "++" represents a degradation rate of 30%-50%, and "+++" represents a degradation rate of 50%-90%, and "++++" means the degradation rate is greater than 90%.

Example 7: Testing the Inhibitory Effect of Formula Compounds on the Proliferation of MCF-7 Cells (Human Breast Cancer Cells) by MTT Assay The inhibitory effect of the compound on the proliferation of MCF-7 cells (commercially available from ATCC) was determined by the MTT method in vitro. The experimental steps were as follows: MCF-7 cells were cultured in 1640 medium of 10% calf serum, seeded in a 96-well plate with $2\times 10^5$ cells/well, and placed in a 37° C., 5% $CO_2$ incubator. Each compound was dissolved in dimethyl sulfoxide (DMSO) to obtain a solution with a concentration of 10 mM, and then diluted to the desired concentration with a phosphate buffer solution. The solution was added to the above 96-well plate. Each concentration has 2 wells with 10 µl per well. Each concentration was tested in duplicate. As a control, DMSO was diluted in the corresponding gradient and then added to the plate. After the 96-well plate was cultured in a 37° C., 5% $CO_2$ cell incubator for 48 hours, 20 µl of MTT solution in 5 mg/ml was added to each well, and it was cultured in the incubator for another 3 to 4 hours. 100 µl of lysate was added to each well and the cells were further incubated overnight in the incubator to fully dissolve the formazan crystals generated. The light absorption value at 492 nm was measured. The relative survival rate of the cells after the compound treatment was calculated based on the light absorption value. The $IC_{50}$ of the compound against MCF-7 cells was calculated by software. The inhibitory effect of synthesized compounds on MCF-7 cells in vitro is shown in the following table:

| Compound No. | IC$_{50}$ (nM) |
|---|---|
| 3 | 80 |
| 8 | 200 |
| 15 | 220 |
| 16 | 300 |
| 21 | 160 |

The above result shows that the synthesized compounds have good inhibitory activity on MCF-7 cells.

Example 8: Testing the Inhibitory Effect of Compounds on the Proliferation of T47D Cell Lines (Human Breast Cancer Cells) by CCK8 Assay The inhibitory effect of the compound on the proliferation of T47D cells (commercially available from ATCC) was determined by the CCK8 method in vitro. The experimental steps were as follows: T47D cells were cultured in 1640 medium of 10% calf serum, seeded in a 96-well plate with $1.5 \times 10^5$/ml, and placed in a 37° C., 5% CO$_2$ incubator. Each compound or the positive drug (Ribociclib) was dissolved in dimethyl sulfoxide (DMSO) to obtain a solution with a concentration of 100 mM, and then diluted to the desired concentration with the culture medium. The solutions were then added to the above 96-well plates. Each concentration has 3 wells with 50 μl per well. As a control, DMSO was diluted in the corresponding gradient and then added to the plate. After the 96-well plate was cultured in a 37° C., 5% CO$_2$ cell incubator for 72 hours, 110 μl of CCK8 solution in 9% was added to each well, and it was cultured in the incubator for another 4 hours. The light absorption value at 450 nm was measured. The relative survival rate of the cells after the compound treatment was calculated based on the light absorption value. The IC$_{50}$ of the compound against T47D cells was calculated by software. The inhibitory effect of synthesized compounds on proliferation of T47D cells in vitro is shown in the following table:

| Compound No. | IC$_{50}$ (μM) |
|---|---|
| 3 | 13.7 |
| 18 | 8.1 |
| The positive drug (Ribociclib) | 68.7 |

The above result shows that the synthesized compounds have good inhibitory activity on proliferation of T47D cells.

All publications mentioned herein are incorporated by reference as if each individual document is cited as a reference, as in the present application. It should also be understood that, after reading the above teachings of the present invention, those skilled in the art can make various changes or modifications, equivalents of which falls in the scope of claims as defined in the appended claims.

The invention claimed is:
1. A compound represented by formula I:

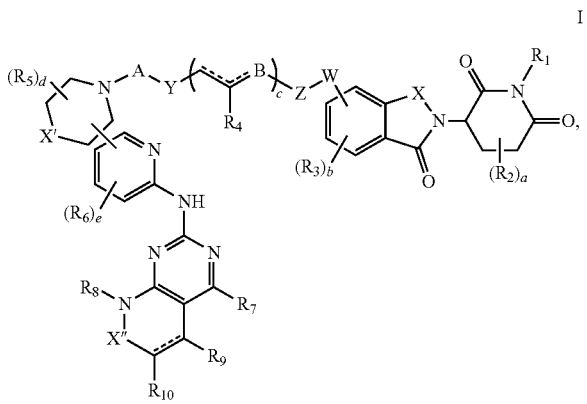

or a pharmaceutically acceptable salt thereof,
wherein:
each ===== is independently a single or double bond;
A is absent;
W is —NR$_{17}$— or —X$_2$C(O)X$_3$—;
X is —C(O)—;
X' is —N—;
X" is absent;
X$_2$ is absent;
X$_3$ is —NR$_{18}$—;
X$_6$ is absent;
Y is —(CR$_{22}$R$_{23}$)$_h$—;
Z is —(CR$_{24}$R$_{25}$)$_i$—;
R$_1$ is H, C$_{1-8}$ alkyl, C$_{2-8}$ alkenyl, C$_{2-8}$ alkynyl, C(O)H, C(O)C$_{1-6}$ hydrocarbyl, C$_{3-8}$ cycloalkyl, C$_{3-8}$ cycloalkenyl, C$_{1-8}$ heterocyclic hydrocarbyl, or phenyl, wherein the C$_{1-8}$ heterocyclic hydrocarbyl contains one or more heteroatoms independently selected from the group consisting of nitrogen, oxygen, and sulfur, and further wherein the C$_{1-8}$ alkyl, C$_{2-8}$ alkenyl, C$_{2-8}$ alkynyl, C(O)C$_{1-6}$ hydrocarbyl, C$_{3-8}$ cycloalkyl, C$_{3-8}$ cycloalkenyl, C$_{1-8}$ heterocyclic hydrocarbyl, or phenyl is optionally substituted;
each R$_2$ is independently H, F, Cl, Br, I, CN, C$_{1-8}$ alkyl, C$_{2-8}$ alkenyl, C$_{2-8}$ alkynyl, C(O)H, C(O)C$_{1-6}$ hydrocarbyl, C(O)NH$_2$, C(O)NHC$_{1-6}$ hydrocarbyl, C(O)N(C$_{1-6}$ hydrocarbyl)$_2$, NR$_{27}$R$_{28}$, OR$_{26}$, C$_{3-8}$ cyclic hydrocarbyl, or C$_{1-8}$ heterocyclic hydrocarbyl, wherein each C$_{1-8}$ heterocyclic hydrocarbyl independently contains one or more heteroatoms independently selected from the group consisting of nitrogen, oxygen, and sulfur, and further wherein each C$_{1-8}$ alkyl, C$_{2-8}$ alkenyl, C$_{2-8}$ alkynyl, C(O)C$_{1-6}$ hydrocarbyl, C(O)NHC$_{1-6}$ hydrocarbyl, C(O)N(C$_{1-6}$ hydrocarbyl)$_2$, C$_{3-8}$ cyclic hydrocarbyl, and C$_{1-8}$ heterocyclic hydrocarbyl is optionally and independently substituted;
each R$_3$ is independently H, F, Cl, Br, I, CN, NO$_2$, C$_{1-8}$ alkyl, C$_{2-8}$ alkenyl, C$_{2-8}$ alkynyl, NR$_{30}$R$_{31}$, OR$_{29}$, X$_6$C(O)$_j$R$_{33}$, X$_6$S(O)$_j$R$_{32}$, cyclic hydrocarbyl, or heterocyclic hydrocarbyl, wherein each heterocyclic hydrocarbyl independently contains one or more heteroatoms independently selected from the group consisting of nitrogen, oxygen, and sulfur, and further wherein each C$_{1-8}$ alkyl, C$_{2-8}$ alkenyl, C$_{2-8}$ alkynyl, cyclic hydrocarbyl, and heterocyclic hydrocarbyl is optionally and independently substituted;
each R$_5$ is independently Fl, F, Cl, Br, I, CN, C$_{1-8}$ alkyl, C$_{2-8}$ alkenyl, C$_{2-8}$ alkynyl, C(O)H, C(O)C$_{1-6}$ hydrocarbyl, C(O)NH$_2$, C(O)NHC$_{1-6}$ hydrocarbyl, C(O)N(C$_{1-6}$ hydrocarbyl)$_2$, NR$_{27}$R$_{28}$, OR$_{26}$, C$_{3-8}$ cyclic hydrocarbyl, or C$_{1-8}$ heterocyclic hydrocarbyl, wherein each C$_{1-8}$ heterocyclic hydrocarbyl independently contains one or more heteroatoms independently selected from the group consisting of nitrogen, oxygen, and sulfur, and further wherein each C$_{1-8}$ alkyl, C$_{2-8}$ alkenyl, C$_{2-8}$ alkynyl, C(O)C$_{1-6}$ hydrocarbyl, C(O)NHC$_{1-6}$ hydrocarbyl, C(O)N(C$_{1-6}$ hydrocarbyl)$_2$, C$_{3-8}$ cyclic hydrocarbyl, and C$_{1-8}$ heterocyclic hydrocarbyl is optionally and independently substituted;

each R$_6$ is independently H, F, Cl, Br, I, CN, NO$_2$, C$_{1-8}$ alkyl, C$_{2-8}$ alkenyl, C$_{2-8}$ alkynyl, NR$_{30}$R$_{31}$, OR$_{29}$, X$_6$C(O)$_j$R$_{33}$, X$_6$S(O)$_j$R$_{32}$, cyclic hydrocarbyl, or heterocyclic hydrocarbyl, wherein each heterocyclic hydrocarbyl independently contains one or more heteroatoms independently selected from the group consisting of nitrogen, oxygen, and sulfur, and further wherein each C$_{1-8}$ alkyl, C$_{2-8}$ alkenyl, C$_{2-8}$ alkynyl, cyclic hydrocarbyl, or heterocyclic hydrocarbyl is optionally and independently substituted;

R$_7$ is H, F, Cl, Br, I, CN, NO$_2$, C$_{1-8}$ alkyl, C$_{2-8}$ alkenyl, C$_{2-8}$ alkynyl, NR$_{30}$R$_{31}$, OR$_{29}$, X$_6$C(O)$_j$R$_{33}$, X$_6$S(O)$_j$R$_{32}$, cyclic hydrocarbyl, or heterocyclic hydrocarbyl, wherein the heterocyclic hydrocarbyl contains one or more heteroatoms independently selected from the group consisting of nitrogen, oxygen, and sulfur, and further wherein the C$_{1-8}$ alkyl, C$_{2-8}$ alkenyl, C$_{2-8}$ alkynyl, cyclic hydrocarbyl, or heterocyclic hydrocarbyl is optionally substituted;

R$_8$ is C$_{3-8}$ cycloalkyl or C$_{3-8}$ cycloalkenyl, wherein the C$_{3-8}$ cycloalkyl or C$_{3-8}$ cycloalkenyl is optionally substituted;

R$_9$ is FI, F, Cl, Br, I, CN, NO$_2$, C$_{1-8}$ alkyl, C$_{2-8}$ alkenyl, C$_{2-8}$ alkynyl, NR$_{30}$R$_{31}$, OR$_{29}$, X$_6$C(O)$_j$R$_{33}$, X$_6$S(O)$_j$R$_{32}$, cyclic hydrocarbyl, or heterocyclic hydrocarbyl, wherein the heterocyclic hydrocarbyl contains one or more heteroatoms independently selected from the group consisting of nitrogen, oxygen, and sulfur, and further wherein the C$_{1-8}$ alkyl, C$_{2-8}$ alkenyl, C$_{2-8}$ alkynyl, cyclic hydrocarbyl, or heterocyclic hydrocarbyl is optionally substituted;

R$_{10}$ is X$_6$C(O)NH$_2$, X$_6$C(O)NH(C$_{1-6}$ alkyl), or X$_6$C(O)N(C$_{1-6}$ alkyl)$_2$;

R$_{17}$ is H, C$_{1-8}$ alkyl, C$_{2-8}$ alkenyl, C$_{2-8}$ alkynyl, C$_{3-8}$ cycloalkyl, C$_{3-8}$ cycloalkenyl, C$_{1-8}$ heterocyclic hydrocarbyl, or phenyl, wherein the C$_{1-8}$ heterocyclic hydrocarbyl contains one or more heteroatoms independently selected from the group consisting of nitrogen, oxygen, and sulfur, and further wherein the C$_{1-8}$ alkyl, C$_{2-8}$ alkenyl, C$_{2-8}$ alkynyl, C$_{3-8}$ cycloalkyl, C$_{3-8}$ cycloalkenyl, C$_{1-8}$ heterocyclic hydrocarbyl, or phenyl is optionally substituted;

R$_{18}$ is H, C$_{1-8}$ alkyl, C$_{2-8}$ alkenyl, C$_{2-8}$ alkynyl, C$_{3-8}$ cycloalkyl, C$_{3-8}$ cycloalkenyl, C$_{1-8}$ heterocyclic hydrocarbyl, or phenyl, wherein the C$_{1-8}$ heterocyclic hydrocarbyl contains one or more heteroatoms independently selected from the group consisting of nitrogen, oxygen, and sulfur, and further wherein the C$_{1-8}$ alkyl, C$_{2-8}$ alkenyl, C$_{2-8}$ alkynyl, C$_{3-8}$ cycloalkyl, C$_{3-8}$ cycloalkenyl, C$_{1-8}$ heterocyclic hydrocarbyl, or phenyl is optionally substituted;

each R$_{22}$ is independently H, CN, C$_{1-8}$ alkyl, C$_{2-8}$ alkenyl, C$_{2-8}$ alkynyl, NH$_2$, NH(C$_{1-6}$ alkyl), N(C$_{1-6}$ alkyl)$_2$, OH, OC$_{1-8}$ alkyl, OC$_{2-8}$ alkenyl, OC$_{2-8}$ alkynyl, OC$_{3-8}$ cycloalkyl, OC$_{3-8}$ cycloalkenyl, Ophenyl, C$_{3-8}$ cycloalkyl, C$_{3-8}$ cycloalkenyl, C$_{1-8}$ heterocyclic hydrocarbyl, or phenyl, wherein each C$_{1-8}$ heterocyclic hydrocarbyl independently contains one or more heteroatoms independently selected from the group consisting of nitrogen, oxygen, and sulfur, and further wherein each C$_{1-8}$ alkyl, C$_{2-8}$ alkenyl, C$_{2-8}$ alkynyl, OC$_{1-8}$ alkyl, OC$_{2-8}$ alkenyl, OC$_{2-8}$ alkynyl, OC$_{3-8}$ cycloalkyl, OC$_{3-8}$ cycloalkenyl, Ophenyl, C$_{3-8}$ cycloalkyl, C$_{3-8}$ cycloalkenyl, C$_{1-8}$ heterocyclic hydrocarbyl, and phenyl is optionally and independently substituted;

each R$_{23}$ is independently H, CN, C$_{1-8}$ alkyl, C$_{2-8}$ alkenyl, C$_{2-8}$ alkynyl, NH$_2$, NH(C$_{1-6}$ alkyl), N(C$_{1-6}$ alkyl)$_2$, OH, OC$_{1-8}$ alkyl, OC$_{2-8}$ alkenyl, OC$_{2-8}$ alkynyl, OC$_{3-8}$ cycloalkyl, OC$_{3-8}$ cycloalkenyl, Ophenyl, C$_{3-8}$ cycloalkyl, C$_{3-8}$ cycloalkenyl, C$_{1-8}$ heterocyclic hydrocarbyl, or phenyl, wherein each C$_{1-8}$ heterocyclic hydrocarbyl independently contains one or more heteroatoms independently selected from the group consisting of nitrogen, oxygen, and sulfur, and further wherein each C$_{1-8}$ alkyl, C$_{2-8}$ alkenyl, C$_{2-8}$ alkynyl, OC$_{1-8}$ alkyl, OC$_{2-8}$ alkenyl, OC$_{2-8}$ alkynyl, OC$_{3-8}$ cycloalkyl, OC$_{3-8}$ cycloalkenyl, Ophenyl, C$_{3-8}$ cycloalkyl, C$_{3-8}$ cycloalkenyl, C$_{1-8}$ heterocyclic hydrocarbyl, and phenyl is optionally and independently substituted;

each R$_{24}$ is independently H, CN, C$_{1-8}$ alkyl, C$_{2-8}$ alkenyl, C$_{2-8}$ alkynyl, NH$_2$, NH(C$_{1-6}$ alkyl), N(C$_{1-6}$ alkyl)$_2$, OH, OC$_{1-8}$ alkyl, OC$_{2-8}$ alkenyl, OC$_{2-8}$ alkynyl, OC$_{3-8}$ cycloalkyl, OC$_{3-8}$ cycloalkenyl, Ophenyl, C$_{3-8}$ cycloalkyl, C$_{3-8}$ cycloalkenyl, C$_{1-8}$ heterocyclic hydrocarbyl, or phenyl, wherein each C$_{1-8}$ heterocyclic hydrocarbyl independently contains one or more heteroatoms independently selected from the group consisting of nitrogen, oxygen, and sulfur, and further wherein each C$_{1-8}$ alkyl, C$_{2-8}$ alkenyl, C$_{2-8}$ alkynyl, OC$_{1-8}$ alkyl, OC$_{2-8}$ alkenyl, OC$_{2-8}$ alkynyl, OC$_{3-8}$ cycloalkyl, OC$_{3-8}$ cycloalkenyl, Ophenyl, C$_{3-8}$ cycloalkyl, C$_{3-8}$ cycloalkenyl, C$_{1-8}$ heterocyclic hydrocarbyl, and phenyl is optionally and independently substituted;

each R$_{25}$ is independently H, CN, C$_{1-8}$ alkyl, C$_{2-8}$ alkenyl, C$_{2-8}$ alkynyl, NH$_2$, NH(C$_{1-6}$ alkyl), N(C$_{1-6}$ alkyl)$_2$, OH, OC$_{1-8}$ alkyl, OC$_{2-8}$ alkenyl, OC$_{2-8}$ alkynyl, OC$_{3-8}$ cycloalkyl, OC$_{3-8}$ cycloalkenyl, Ophenyl, C$_{3-8}$ cycloalkyl, C$_{3-8}$ cycloalkenyl, C$_{1-8}$ heterocyclic hydrocarbyl, or phenyl, wherein each C$_{1-8}$ heterocyclic hydrocarbyl independently contains one or more heteroatoms independently selected from the group consisting of nitrogen, oxygen, and sulfur, and further wherein each C$_{1-8}$ alkyl, C$_{2-8}$ alkenyl, C$_{2-8}$ alkynyl, OC$_{1-8}$ alkyl, OC$_{2-8}$ alkenyl, OC$_{2-8}$ alkynyl, OC$_{3-8}$ cycloalkyl, OC$_{3-8}$ cycloalkenyl, Ophenyl, C$_{3-8}$ cycloalkyl, C$_{3-8}$ cycloalkenyl, C$_{1-8}$ heterocyclic hydrocarbyl, and phenyl is optionally and independently substituted;

each R$_{26}$ is independently H, C$_{1-8}$ alkyl, C$_{2-8}$ alkenyl, C$_{2-8}$ alkynyl, C$_{3-8}$ cyclic hydrocarbyl, or C$_{1-8}$ heterocyclic hydrocarbyl, wherein each C$_{1-8}$ heterocyclic hydrocarbyl independently contains one or more heteroatoms independently selected from the group consisting of nitrogen, oxygen, and sulfur, and further wherein each C$_{1-8}$ alkyl, C$_{2-8}$ alkenyl, C$_{2-8}$ alkynyl, C$_{3-8}$ cyclic hydrocarbyl, and C$_{1-8}$ heterocyclic hydrocarbyl is optionally and independently substituted;

each R$_{27}$ is independently H, C$_{1-8}$ alkyl, C$_{2-8}$ alkenyl, C$_{2-8}$ alkynyl, C$_{3-8}$ cyclic hydrocarbyl, or C$_{1-8}$ heterocyclic hydrocarbyl, wherein each C$_{1-8}$ heterocyclic hydrocarbyl independently contains one or more heteroatoms independently selected from the group consisting of nitrogen, oxygen, and sulfur, and further wherein each C$_{1-8}$ alkyl, C$_{2-8}$ alkenyl, C$_{2-8}$ alkynyl, C$_{3-8}$ cyclic hydrocarbyl, and $C_{1-8}$ heterocyclic hydrocarbyl is optionally and independently substituted;

each $R_{28}$ is independently H, $C_{1-8}$ alkyl, $C_{2-8}$ alkenyl, $C_{2-8}$ alkynyl, $C_{3-8}$ cyclic hydrocarbyl, or $C_{1-8}$ heterocyclic hydrocarbyl, wherein each $C_{1-8}$ heterocyclic hydrocarbyl independently contains one or more heteroatoms independently selected from the group consisting of nitrogen, oxygen, and sulfur, and further wherein each $C_{1-8}$ alkyl, $C_{2-8}$ alkenyl, $C_{2-8}$ alkynyl, $C_{3-8}$ cyclic hydrocarbyl, and $C_{1-8}$ heterocyclic hydrocarbyl is optionally and independently substituted;

each $R_{29}$ is independently H, $C_{1-8}$ alkyl, $C_{2-8}$ alkenyl, $C_{2-8}$ alkynyl, $NH_2$, $NH(C_{1-6}$ alkyl), $N(C_{1-6}$ alkyl$)_2$, $C_{3-8}$ cyclic hydrocarbyl, or $C_{1-8}$ heterocyclic hydrocarbyl, wherein each $C_{1-8}$ heterocyclic hydrocarbyl contains one or more heteroatoms independently selected from the group consisting of nitrogen, oxygen, and sulfur, and further wherein each $C_{1-8}$ alkyl, $C_{2-8}$ alkenyl, $C_{2-8}$ alkynyl, $C_{3-8}$ cyclic hydrocarbyl, and $C_{1-8}$ heterocyclic hydrocarbyl is optionally and independently substituted;

each $R_{30}$ is independently H, $C_{1-8}$ alkyl, $C_{2-8}$ alkenyl, $C_{2-8}$ alkynyl, $NH_2$, $NH(C_{1-6}$ alkyl), $N(C_{1-6}$ alkyl$)_2$, $C_{3-8}$ cyclic hydrocarbyl, or $C_{1-8}$ heterocyclic hydrocarbyl, wherein each $C_{1-8}$ heterocyclic hydrocarbyl contains one or more heteroatoms independently selected from the group consisting of nitrogen, oxygen, and sulfur, and further wherein each $C_{1-8}$ alkyl, $C_{2-8}$ alkenyl, $C_{2-8}$ alkynyl, $C_{3-8}$ cyclic hydrocarbyl, and $C_{1-8}$ heterocyclic hydrocarbyl is optionally and independently substituted;

each $R_{31}$ is independently H, $C_{1-8}$ alkyl, $C_{2-8}$ alkenyl, $C_{2-8}$ alkynyl, $NH_2$, $NH(C_{1-6}$ alkyl), $N(C_{1-6}$ alkyl$)_2$, $C_{3-8}$ cyclic hydrocarbyl, or $C_{1-8}$ heterocyclic hydrocarbyl, wherein each $C_{1-8}$ heterocyclic hydrocarbyl contains one or more heteroatoms independently selected from the group consisting of nitrogen, oxygen, and sulfur, and further wherein each $C_{1-8}$ alkyl, $C_{2-8}$ alkenyl, $C_{2-8}$ alkynyl, $C_{3-8}$ cyclic hydrocarbyl, and $C_{1-8}$ heterocyclic hydrocarbyl is optionally and independently substituted;

each $R_{32}$ is independently H, $C_{1-8}$ alkyl, $C_{2-8}$ alkenyl, $C_{2-8}$ alkynyl, $NH_2$, $NH(C_{1-6}$ alkyl), $N(C_{1-6}$ alkyl$)_2$, $C_{3-8}$ cyclic hydrocarbyl, or $C_{1-8}$ heterocyclic hydrocarbyl, wherein each $C_{1-8}$ heterocyclic hydrocarbyl contains one or more heteroatoms independently selected from the group consisting of nitrogen, oxygen, and sulfur, and further wherein each $C_{1-8}$ alkyl, $C_{2-8}$ alkenyl, $C_{2-8}$ alkynyl, $C_{3-8}$ cyclic hydrocarbyl, and $C_{1-8}$ heterocyclic hydrocarbyl is optionally and independently substituted;

each $R_{33}$ is independently H, $C_{1-8}$ alkyl, $C_{2-8}$ alkenyl, $C_{2-8}$ alkynyl, $NH_2$, $NH(C_{1-6}$ alkyl), $N(C_{1-6}$ alkyl$)_2$, $C_{3-8}$ cyclic hydrocarbyl, or $C_{1-8}$ heterocyclic hydrocarbyl, wherein each $C_{1-8}$ heterocyclic hydrocarbyl contains one or more heteroatoms independently selected from the group consisting of nitrogen, oxygen, and sulfur, and further wherein each $C_{1-8}$ alkyl, $C_{2-8}$ alkenyl, $C_{2-8}$ alkynyl, $C_{3-8}$ cyclic hydrocarbyl, and $C_{1-8}$ heterocyclic hydrocarbyl is optionally and independently substituted;

a is 0, 1, 2, 3, 4, or 5;
b is 0, 1, 2, or 3;
c is 0;
d is 0, 1, 2, 3, 4, 5, 6, 7, 8, or 9;
e is 0, 1, 2, or 3;
h is 0, 1, 2, 3, 4, 5, or 6;
i is 1, 2, 3, 4, 5, or 6; and
j is 0, 1, or 2;

wherein the optional substituents for $R_1$, $R_2$, $R_3$, $R_5$, $R_6$, $R_7$, $R_8$, $R_9$, $R_{17}$, $R_{18}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, and $R_{33}$ are independently selected from the group consisting of F, Cl, Br, I, CN, $C_{1-6}$ halohydrocarbyl, C(O)H, C(O)$C_{1-6}$ hydrocarbyl, $NH_2$, NH($C_{1-6}$ hydrocarbyl), N($C_{1-6}$ hydrocarbyl$)_2$, OH, O($C_{1-6}$ hydrocarbyl), and S(O)$_2C_{1-6}$ hydrocarbyl.

2. The compound according to claim 1, wherein the compound is represented by formula I:

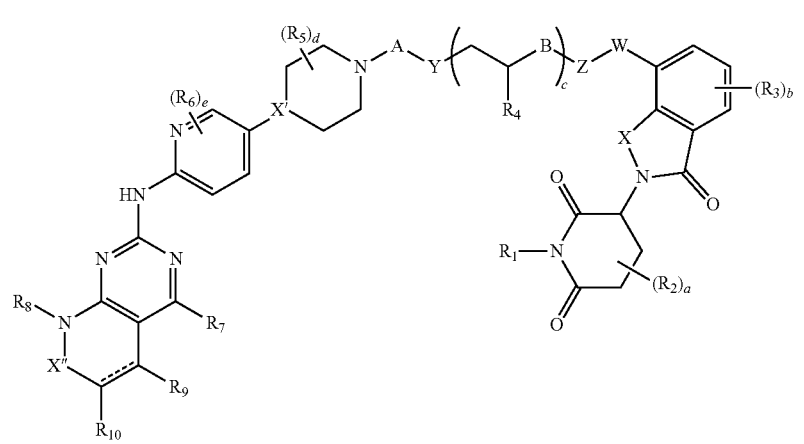

or a pharmaceutically acceptable salt thereof.

3. The compound according to claim 1, or a pharmaceutically acceptable salt thereof, wherein:
$R_1$ is H, $C_{1-4}$ alkyl, or $C_{3-5}$ cycloalkyl, wherein the $C_{1-4}$ alkyl or $C_{3-5}$ cycloalkyl is optionally substituted; and
$R_8$ is $C_{3-8}$ cycloalkyl, wherein the $C_{3-8}$ cycloalkyl is optionally substituted.

4. The compound according to claim 1, or a pharmaceutically acceptable salt thereof, wherein:
W is —$X_2$C(O)$X_3$—;
each $R_{22}$ is independently H, $C_{1-4}$ alkyl, $C_{2-4}$ alkenyl, $C_{2-4}$ alkynyl, OH, $C_{3-4}$ cycloalkyl, or $C_{3-4}$ cycloalkenyl, wherein each $C_{1-4}$ alkyl, $C_{2-4}$ alkenyl, $C_{2-4}$ alkynyl, $C_{3-4}$ cycloalkyl, and $C_{3-4}$ cycloalkenyl is optionally and independently substituted;

each $R_{23}$ is independently H, $C_{1-4}$ alkyl, $C_{2-4}$ alkenyl, $C_{2-4}$ alkynyl, OH, $C_{3-4}$ cycloalkyl, or $C_{3-4}$ cycloalkenyl, wherein each $C_{1-4}$ alkyl, $C_{2-4}$ alkenyl, $C_{2-4}$ alkynyl, $C_{3-4}$ cycloalkyl, and $C_{3-4}$ cycloalkenyl is optionally and independently substituted;

each $R_{24}$ is independently H, $C_{1-4}$ alkyl, $C_{2-4}$ alkenyl, $C_{2-4}$ alkynyl, OH, $C_{3-4}$ cycloalkyl, or $C_{3-4}$ cycloalkenyl, wherein each $C_{1-4}$ alkyl, $C_{2-4}$ alkenyl, $C_{2-4}$ alkynyl, $C_{3-4}$ cycloalkyl, and $C_{3-4}$ cycloalkenyl is optionally and independently substituted;

each $R_{25}$ is independently H, $C_{1-4}$ alkyl, $C_{2-4}$ alkenyl, $C_{2-4}$ alkynyl, OH, $C_{3-4}$ cycloalkyl, or $C_{3-4}$ cycloalkenyl, wherein each $C_{1-4}$ alkyl, $C_{2-4}$ alkenyl, $C_{2-4}$ alkynyl, $C_{3-4}$ cycloalkyl, and $C_{3-4}$ cycloalkenyl is optionally and independently substituted; and h is 1, 2, 3, 4, 5, or 6.

5. The compound according to claim 1, wherein the compound is selected from the group consisting of:

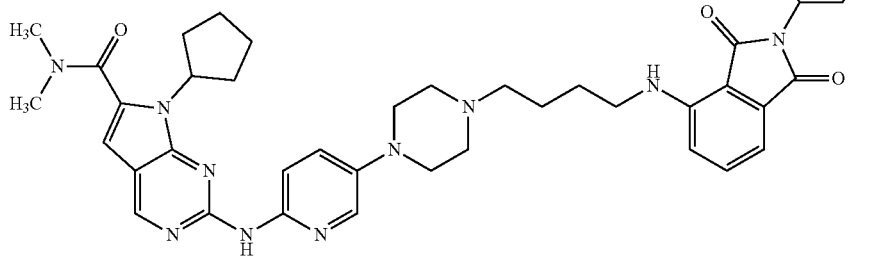

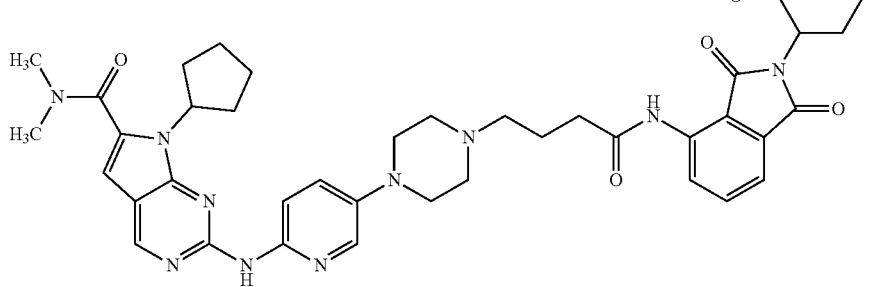

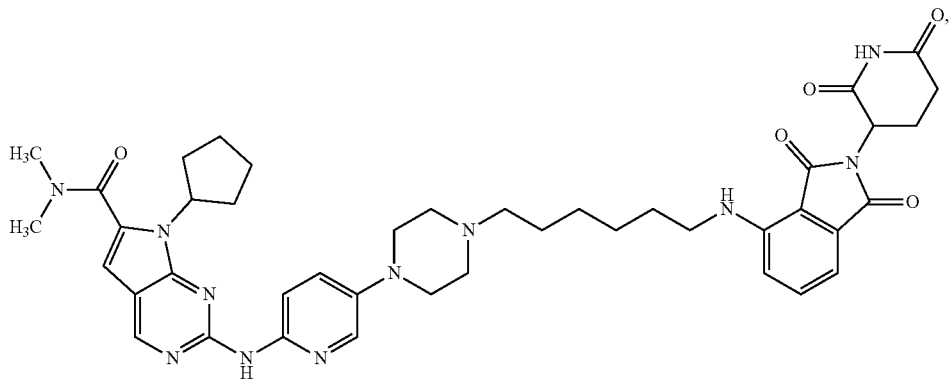

-continued

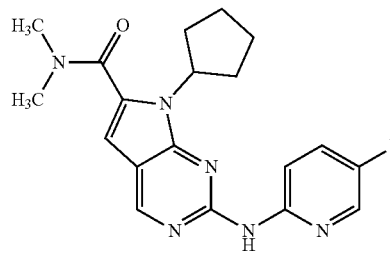
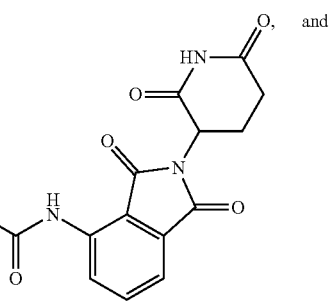

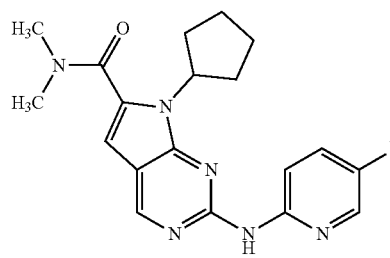
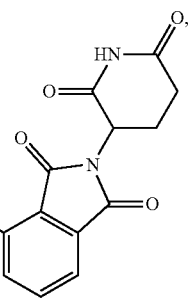

or a pharmaceutically acceptable salt thereof.

6. A medicament comprising the compound according to claim 1, or a pharmaceutically acceptable salt thereof.

7. A pharmaceutical composition comprising a pharmaceutically acceptable carrier and the compound according to claim 1, or a pharmaceutically acceptable salt thereof.

8. A method for inhibiting cyclin dependent kinase activity in a subject, wherein the method comprises administering to the subject in need thereof a therapeutically effective amount of a compound according to claim 1, or a pharmaceutically acceptable salt thereof.

9. The method according to claim 8, wherein the subject has a tumor or an autoimmune disease.

10. A method for inhibiting cyclin dependent kinase activity in a subject, wherein the method comprises administering to the subject in need thereof a therapeutically effective amount of the pharmaceutical composition according to claim 7.

11. The method according to claim 10, wherein the subject has a tumor or an autoimmune disease.

12. A method for inhibiting tumor cell proliferation in a subject, wherein the method comprises administering to the subject in need thereof a therapeutically effective amount of a compound according to claim 1, or a pharmaceutically acceptable salt thereof.

13. A method for inhibiting tumor cell proliferation in a subject, wherein the method comprises administering to the subject in need thereof a therapeutically effective amount of the pharmaceutical composition according to claim 7.

* * * * *